(12) United States Patent
Zhang et al.

(10) Patent No.: US 8,785,180 B2
(45) Date of Patent: Jul. 22, 2014

(54) BIOCHEMICAL REACTOR

(75) Inventors: Siliang Zhang, Shanghai (CN); Yuefang Zhang, Shanghai (CN); Jian Liu, Shanghai (CN); Xujun Yuan, Shanghai (CN); Meijin Guo, Shanghai (CN); Liqing He, Shanghai (CN); Gongjian Chen, Shanghai (CN); Ming Zhang, Shanghai (CN); Guoqiang Sun, Shanghai (CN); Wenfeng Ma, Shanghai (CN); Ju Chu, Shanghai (CN); Yingping Zhuang, Shanghai (CN); Yonghong Wang, Shanghai (CN); Mingzhi Huang, Shanghai (CN); Haifeng Hang, Shanghai (CN); Jianye Xia, Shanghai (CN)

(73) Assignees: Shanghai Guoqiang Bioengineering Equipment Co., Ltd., Shanghai (CN); Shanghai Cohere Electronics Technology Co., Ltd., Shanghai (CN); East China University of Science and Technology, Shanghai (CN)

( * ) Notice: Subject to any disclaimer, the term of this patent is extended or adjusted under 35 U.S.C. 154(b) by 488 days.

(21) Appl. No.: 12/871,539

(22) Filed: Aug. 30, 2010

(65) Prior Publication Data

US 2012/0015391 A1    Jan. 19, 2012

Related U.S. Application Data

(63) Continuation of application No. 12/665,604, filed as application No. PCT/CN2008/071348 on Jun. 18, 2008, now abandoned.

(30) Foreign Application Priority Data

Jun. 18, 2007 (CN) .................... 2007 2 0071207 U

(51) Int. Cl.
| | |
|---|---|
| C12M 1/34 | (2006.01) |
| C12M 3/00 | (2006.01) |
| G01N 21/64 | (2006.01) |
| G01N 21/25 | (2006.01) |
| C12M 1/00 | (2006.01) |
| C12M 1/06 | (2006.01) |

(52) U.S. Cl.
CPC .......... *G01N 21/6428* (2013.01); *G01N 21/253* (2013.01); *C12M 41/06* (2013.01); *C12M 27/02* (2013.01)
USPC ......................................... 435/288.7; 435/29

(58) Field of Classification Search
CPC  C12M 41/36; C12M 1/3446; G01N 21/8507; G01N 21/6428; G01N 21/6452; G01N 21/253; G01N 15/1475; C12Q 1/04; G06T 7/0012; G06T 2207/30072; G06T 2207/10056; G06K 9/00
USPC ................... 435/29, 288.7; 359/368, 382, 392
See application file for complete search history.

(56) References Cited

U.S. PATENT DOCUMENTS

| | | | | |
|---|---|---|---|---|
| 6,800,452 | B1* | 10/2004 | McNeil et al. | 435/29 |
| 6,809,862 | B2 | 10/2004 | Behnsen et al. | |
| 2003/0147132 | A1* | 8/2003 | Behnsen et al. | 359/368 |
| 2003/0186227 | A1* | 10/2003 | Balasubramanian et al. | 435/6 |
| 2009/0104594 | A1* | 4/2009 | Webb | 435/3 |

FOREIGN PATENT DOCUMENTS

| | | | |
|---|---|---|---|
| CN | 1110316 | 10/1995 | |
| CN | 1312368 | 9/2001 | |
| CN | 1369701 | 9/2002 | |
| CN | 1971333 | 6/2006 | |
| CN | 101071106 | 11/2007 | |
| CN | 201047885 | 4/2008 | |
| DE | 4032002 A1 * | 6/1991 | ............... C12M 1/34 |
| DE | 10350243 | 5/2005 | |
| WO | 2006/061947 | 6/2006 | |

OTHER PUBLICATIONS

Machine translation of DE4032002A1. Aug. 30, 2012.*
Machine translation of CN1312368. Aug. 30, 2012.*

Machine Translation of CN 101071106. Translated on Mar. 11, 2013.*
International Search Report of PCT/CN2008/071348, dated Oct. 16, 2008.
Written Opinion of the International Searching Authority of PCT/CN2008/071348, dated Oct. 16, 2008.

* cited by examiner

*Primary Examiner* — Michael Hobbs
(74) *Attorney, Agent, or Firm* — Hamre, Schumann, Mueller & Larson, P.C.

(57) ABSTRACT

A biochemical reactor involves an online cell examination microscope thereon. The online cell examination microscope comprises a main body, an objective lens, an observation entrance window, a sampling device, an external light source system. Said observation entrance window lies in front of said main body and the sampling device lies in front of said observation entrance window. An objective lens and said external light source system lie behind the observation entrance window in the main body. A reflector prism is installed between the external light source system and the objective lens. A reflector lies behind the objective lens and in front of the observation entrance window. An annular diaphragm is placed in front of the reflecting prism. A CCD or an area image sensor is arranged on the upper side of the reflectance prism.

12 Claims, 19 Drawing Sheets

B

US 8,785,180 B2

BIOCHEMICAL REACTOR

TECHNICAL FIELD

The invention relates to a biochemical reactor, in particularly, to a biochemical reactor, which is equipped with an in-situ cell examination microscope thereon. The invention also relates to a biochemical reactor, which is equipped with an in-situ cell examination microscope thereon and can be used in parameter correlation analysis based on the multi-scale theory.

BACKGROUND ART

When the product is prepared by cell cultivation during bioprocess, the growth and the cellmorphology which are customarily sampled from the tank and then observed by an off-line microscope, are very important monitoring parameters. Recently, quantified information on the growth and the morphology may be obtained with the development of electronic technique, which enables the conversion of images into digital signals to be processed by a computer. However, the foregoing methods merely make use of off-line sampling and therefore no dynamic observation can be made. Particularly, in the case of large scale animal cells cultivation, wherein prevention of foreign microbes from contamination is the primary concern in the process, therefore, frequent sampling should be avoided. In such a case, it will result in poor dynamic observation and difficult process analysis.

Thus, there is an urgent need in the art for a biochemical reactor, which is equipped with an in-situ cell examination microscope with excellent dynamic observation, high resolution and easy process analysis. An in-situ cell examination microscope which is inserted into a fermenter should meet the following requirements: 1) the resolution and visual field should be suitable for distinguishing bacteria, fungi and animal cells, dead cells and living cells, and conducting a morphological analysis correspondingly; 2) there should be a maximum concentration limit due to variation of cell concentration during the course of cell culture; 3) the problem that microorganisms grow or adhere to the surface of the lens after the probe of the microscope has been inserted into a fermenter for a long time should be overcome; 4) the structure of the microscope should withstand sterilization and sterile operations of the biochemical reactor; 5) the microscope should be able to convert and process real-time digital image signals in real time according to the requirement of the reactor.

An in-situ microscopic device based on fluorescence-excited process is disclosed by Dr Christoph Bittner from Germany. The main working principle of the device is shown in FIG. 1, wherein the monochromatic UV light emitted by a laser is filtered by a lens L1 and a pinhole space, and then passes through two lenses, L2 and L3 before it is reflected by a bichromatic glass onto an object lens which directs the light onto the surfaces of the cells in a biochemical reactor chamber. The fluorescence generated by cells due to fluorescence effect converges at the object lens, passes the bichromatic glass, a reflector and a wave filter in sequence, and finally develops an image in a synchronization camera. Since the cells in the biochemical reactor are rotating at high speed, it is necessary for the synchronization camera to have a very short exposure time, usually less than 2 ms (depending on the magnifying power). The advantage of this process is omission of any complicated mechanical sampling device. However, contrast and resolution for the images of transparent cells are poor due to the bright-field illumination used in this process. Furthermore, since the manner of single-wavelength fluorescence-excitation generated through the excitation of a beam for high-speed photo-shooting is employed, it will cost high to change the stimulating beam wavelength into a different one.

A microscope based on in-situ sampling is disclosed in U.S. Pat. No. 6,809,862 in 2004. As shown in FIG. 2, a sampling window 4 keeps moving to and fro. When the sampling window 4 moves to the place where a microscope 16 and a light source are located, the cell culture in a biochemical reactor 10 will flow into an examination chamber 12. When the sampling window 4 moves to another place, the cell culture in the examination chamber 12 is relatively stable, for micro-examination. To replace the microlens conveniently, a rinsing chamber is designed as shown in FIG. 3. The microlens and the sampling window 4 can be drawn into the rinsing chamber by pulling a rod 2. There are holes 8 in the wall of the rinsing chamber for introducing steam or disinfectant for sterilization or rinsing. The microlens also can be replaced conveniently in-situ. Likewise, contrast and resolution for the images of transparent cells are poor due to the bright-field illumination used in this process. Furthermore, since the illumination system is positioned within the biochemical reactor, it is not convenient to replace the light source and change the wavelength of the excitation light, and unable to distinguish different species of cells, for example, dead cells and living cells. Additionally, frequent sampling and sterilization may contaminate the biological culture process.

An in-situ cell examination microscope is disclosed in DE 10350243 in 2004, which makes use of SLD (Super Light Diode) illumination, multimode fiber transmission and high-speed synchronization shooting. A light beam emitted by a laser or a light emitting diode is transmitted by a multimode fiber into a biochemical reactor to illuminate the cells in the biochemical reactor (the reactor), and the light reflected by the cells converges at an object lens and then develops into an image in a CCD camera. Since the cells continuously move in the biochemical reactor, the exposure time of the camera has to be short enough to achieve an instant capture of a cell image. The images captured by the camera are sent to a computer for processing. Likewise, contrast and resolution for the images of transparent cells are poor due to the bright-field illumination used in this process. High-speed agitation in the biochemical reactor entails the use of a high-speed camera. There is no sampling device herein which may restrict the field depth, the effect of which thus can not be eliminated, just as in the case shown in FIG. 1. Additionally, since a complex SLD (Super Light Diode) is used as the light source, the driving and controlling device of the light source is complicated, resulting in high cost and difficulty in replacing the light source and changing the excitation wavelength.

Apparently, there is an urgent need in the art for a biochemical reactor equipped with an in-situ cell examination microscope with excellent dynamic examination, high resolution and easy process analysis.

On the other hand, it is important to monitor the biomass in the production of living cells. Especially, the advancement in metabolic engineering research has been successfully applied in various fields including microbial breeding, optimization of existing processes, development of new products and environment management. The new trend is to combine the study on fermentation with that on the mechanism of intracellular processes, and to combine sensing technology, computer technology, isotope technology with various detection technologies used in laboratory, so as to make real-time metabolic flux analysis of the processes. However, due to the use of composite culture medium containing solid particles in fermentation and the difficulty in distinguishing dead cells from living ones, the amount of living cells, which is significant for determining a real-time metabolic flow, has to be measured with a manual means used in a laboratory or with an indirect means suffering from a large error. It is urgent to develop a new technical route by combining the in-situ technology for measuring living cell concentration with metabolic flux analysis.

Thus, there is a lack of a biochemical reactor in the art, which is adapted for measuring the amount of living cells therein for correlation analysis.

In addition, a fermentation process is customarily optimized and scaled up on the basis of a static concept wherein extracellular parameters are measured and used to choose the optimal point for process control. This is essentially no more than an extension of the macro-dynamic concept in the field of chemical engineering to the field of fermentation engineering. Along with the intensive development of research on life science, mechanisms of intracellular processes are getting more and more clear. However, the research focused merely on physiological regulation mechanism can usually reveal just a local aspect or a temporary feature of physiological regulation. Highly branched and dispersed research can not play a decisive role in controlling, optimizing and scaling up the whole process of a biochemical reactor. In an attempt to solve the above systematic problems, after studying the characteristics of cellular process in a biochemical reactor, the present inventors have devoted to the study on the multi-scale problem of cellular process, and have provided an optimizing technique based on correlated parameters of a fermentation process at multi-levels and a scaling-up technique based on the adjustment of multiple parameters of a fermentation process.

Along with the intensive development of the foregoing study on basic theories, there is an urgent need for sensing technology and computer technology to follow the development of a process, and to design a new-concept fermenter for the multi-scale study of a biological process. The fermenter is capable of in-situ detecting or controlling multiple parameters based on the monitoring of the material stream in a biochemical reactor. Furthermore, a software package is developed, which is suitable for various reactors, combines various process theories and controlling theories, and could be used for process analysis and optimizing operations of a fermentation process.

On the other hand, there is a lack of a novel biochemical reactor in the art, which is adapted for multi-parameter correlation analysis.

In summary, there is an urgent need in the art for a biochemical reactor equipped with an in-situ cell examination microscope with excellent dynamic examination, high resolution and easy process analysis.

SUMMARY OF THE INVENTION

The first object of the invention is to provide a biochemical reactor with an in-situ cell examination microscope.

The second object of the invention is to improve the contrast and the resolution of the images of cells obtained by the microscope using examination dark field illumination; provide an exterior light source with changeable wavelength; and provide a simply-structured mechanical sampling device as well as an in-situ cell examination microscope suitable for biochemical reactor with easy operation and low cost.

The third object of the invention is to provide a biochemical reactor for parameter correlation analysis under the guidance of the multi-scale theory and a method for optimization and scale-up of a fermentation process, in particular to provide a biochemical reactor which is equipped with an in-situ cell examination microscope and is used to carry out correlation analysis by combining the technique for measuring the amount of living cells with other measuring techniques.

The fourth object of the invention is the use of the biochemical reactor according to the invention in optimizing and scaling up a fermentation process.

In the first aspect of the invention, for solving the foregoing technical problems, the technical solution is provided as follows:

A biochemical reactor with an in-situ cell examination microscope is provided. Said microscope comprises a main body, an objective lens, an observation entrance window, a sampling device and an external light source system. Said observation entrance window lies in front of said main body and the sampling device lies in front of said observation entrance window. Said objective lens and said external light source system lie behind the observation entrance window in the main body. A reflector prism is installed between the external light source system and the objective lens. A reflector lies behind the objective lens and in front of the observation entrance window. An annular diaphragm is placed in front of the reflecting prism. A CCD or an area array image sensor is arranged on upper side of the reflecting prism. The sampling device includes a sampling piece, an elastic element and a mobile device. Said elastic element is installed between the sampling piece and the drive shaft of the mobile device. A space between the head end of the sampling piece and the observation entrance window forms the sampling pool.

In a preferred embodiment, the biochemical reactor is a microbe reactor, an animal cell reactor or a photobiological reactor.

Preferably, the main body of the in-situ cell examination microscope is connected to the biochemical reactor with a locknut, and a gasket is arranged between the main body of the in-situ cell examination microscope and the biochemical reactor for sealing.

In the in-situ cell examination microscope of the biochemical reactor, the exterior light source system consists of a light source, a condenser and a replaceable color filter, wherein the light source is a halogen lamp or a LED lamp, and the light beams emitted by the lamp are focused by the condenser to give parallel beams from which beams in the desired band are obtained after they pass through the replaceable color filter.

In the in-situ cell examination microscope of the biochemical reactor, one form of the movable device consists of a driving axle, a connecting rod, a pulling rod for sampling and a flexible element, wherein the connecting rod equipped with the driving axle is connected to the pulling rod for sampling through a screw, the pulling rod for sampling and the flexible element are welded together on one end face of the flexible element to give a sealed joint, and the main body of the microscope is connected to the other end face of the flexible element by welding.

In the in-situ cell examination microscope of the biochemical reactor, another form of the movable device consists of a driving axle, an electric motor and a sampling tube, wherein the sampling tube is connected to the front end of the main body of the microscope, the electric motor is arranged at the back of the sampling tube, and the output axle of the electric motor is connected to the driving axle.

In the in-situ cell examination microscope of the biochemical reactor, the sampling piece, made from stainless steel or sapphire, consists of three cylinders of different diameters.

After photoelectric conversion in the CCD or the area array image sensor, the resulting digital signals are sent to an image acquisition and processing unit, which then sends the processing results to a computer for analysis, display or store.

In a specific embodiment, a living cell sensor is further arranged on the body of the biochemical reactor.

In a preferred embodiment, the living cell sensor uses a four-electrode system, wherein the protoplast in a living cell acts as electrolyte when the cell is placed in an alternating electric field, and the capacitance resulting from the polarization of the alternating electric field correlates with the biomass. Since different polarizing effects will result from the change of the frequency of the alternating electric field, this can be used to determine the optimal measuring conditions. The capacitance measured as the corresponding signal is sent to a computer for data processing, as the base of the biomass for multi-parameter correlation analysis.

In a specific embodiment, the following components for process optimization and data scale-up are arranged on the body of the biochemical reactor:

A sensing system with apparatuses, instruments and sensors for detecting and controlling multiple parameters, a process pipeline system with installing supports, and an electric control cabinet with industrial personal computers and executing components.

In a specific embodiment, the sensing system with apparatuses, instruments and sensors for detecting and controlling multiple parameters comprises a temperature sensor, a pH sensor, a dissolved oxygen sensor, a whole-tank weight sensor, an exhaust gas $CO_2$ interface, an exhaust gas $O_2$ interface, a speed sensor, a pressure sensor and a defoaming sensor, wherein the multiple parameters include temperature, agitation speed, gas flow rate, tank pressure, defoaming, pH, dissolved oxygen concentration, real volume and weight of a fermentation broth, amount of the supplement (including substrate, precursor, oil, and acidic/basic substance), exhaust gas $CO_2$ and exhaust gas $O_2$.

In a specific embodiment, the process pipeline system with installing supports comprises a feed flask, a preheater, a stand for whole-tank weighing, a special support for sampling, a tank body assembly, a quick detachable bedplate, an electric motor, a pipe rack, an oil-water separator, a pressure reducing valve, a filter, a flowmeter, an air filter, a pressure gauge, a cooler, a pipe sight glass, a water heater, a sampling valve with no dead volume, a defoaming sensor interface, an exhaust gas $CO_2$ interface, an exhaust gas $O_2$ interface, a temperature sensor, a pH sensor interface and a DO sensor interface.

In a specific embodiment, the electric control cabinet with industrial personal computers and executing components comprises a thermal mass flow meter, a peristaltic pump, an electronic balance for supplementing substrate, an electronic balance for precursor or oil, an electronic balance for acidic/basic substance, a circulating pump, an electromagnetic valve, a digital-to-analog converter, a analog-to-digital converter, a local computer, an upper computer, a modem and a rare-earth motor.

In a preferred embodiment, computer softwares are used in the electric control cabinet with industrial personal computers and executing components to effect in-situ acquisition of parameters, off-line computation of parameters, data recording and in-situ control of part? of parameters according to the need of field data acquisition and handling as well as the requirement of process optimization, and to send all data concerning the parameters synchronously to the upper computer via a local area network, wherein the upper and local computers are programmed using configuration language and C language, and simple redundancy technology is used in data recording.

In the second aspect of the invention, in order to solve the foregoing technical problems, a technical solution is provided as follows:

An in-situ cell examination microscope is provided. Said microscope comprises a main body, an objective lens, an observation entrance window, an sampling device and an external light source system. Said observation entrance window lies in the front of said main body and the sampling device lies in front of said observation entrance window. Said objective lens and said external light source system lie behind the observation entrance window in the main body. A reflector prism is installed between the external light source system and the objective lens. A reflector lies behind the objective lens and in front of the observation entrance window. An annular diaphragm is placed in front of the reflecting prism. A CCD or an area array image sensor is arranged on the upper side of reflecting prism. The sampling device includes a sampling piece, an elastic element and a mobile device. Said elastic element is installed between the sampling piece and the drive shaft of the mobile device. A space between the head end of the sampling piece and the observation entrance window forms the sampling pool.

In the second aspect of the invention, for solving the foregoing technical problems, a technical solution is provided as follows:

A fermentation process using the biochemical reactor of the invention, comprising the following steps:

(a) Measuring the physiological metabolic parameters, the characteristics associated with the physiological metabolic parameters or combinations thereof, wherein the physiological metabolic parameters are selected from dissolved oxygen, oxygen uptake rate, pH, $CO_2$ evolution rate, respiratory quotient, the amount of living cells or cell morphology, the metabolic product(s) to be measured, substrate consumption, or combinations thereof;

(b) Comparing the physiological metabolic parameters, the characteristics associated with the physiological metabolic parameters or combinations thereof as measured in step (a) with those having predetermined values, choosing a biochemical reactor bearing measurements closest to the predetermined values, and thus determining a reactor that is optimized and scaled-up accordingly;

wherein the physiological metabolic parameters are defined in step (a).

In a preferred embodiment, the metabolic product(s) or the substrate consumption as measured are those measured manually in a laboratory.

In a preferred embodiment, the biochemical reactor is selected from a fermenter for vitamin $B_{12}$ or cephalothin.

In a preferred embodiment, the biochemical reactor is a fermenter of 20-2000 $m^3$.

In a specific embodiment, in Step (a), the physiological metabolic parameters, the characteristics associated with the physiological metabolic parameters or combinations thereof are obtained by detecting several process control parameters of the biochemical reactor, wherein the several process control parameters are temperature, agitation speed, gas flow rate, tank pressure, defoaming, pH, dissolved oxygen concentration, real volume and weight of a fermentation liquor, amount of the supplement (including substrate, precursor, oil, and acidic/basic substance), exhaust gas $CO_2$ and exhaust gas $O_2$.

Specifically, for example, the oxygen uptake rate (OUR) is obtained by measuring the concentration of exhaust gas $O_2$, the gas flow rate, the volume of the fermentation broth; and more specifically, for example, by using the following equation:

$$OUR = \frac{F_{in}}{V}\left[C_{O_2 in} - \frac{C_{in\,in} \cdot C_{O_2 in}}{1 - (C_{O_2 out} + C_{CO_2 out})}\right] \cdot f$$

wherein:

$F_{in}$: inlet gas flow, (mol)

$C_{in.in}\backslash C_{O2.in}\backslash C_{CO2.in}$: concentrations of inert gas, oxygen and carbon dioxide in the inlet gas, respectively, % (V)

$C_{O2.out}\backslash C_{CO2.out}$: concentrations of oxygen and carbon dioxide in the outlet gas, respectively, % (V)

V: volume of the fermentation broth, (L)

f is calculated through the following equation:

$$f = \frac{273}{273 + t_{in}} \cdot P_{in} \cdot \frac{1}{1+h} \times 10^{-5}$$

wherein:

$P_{in}$: absolute pressure of inlet gas, Pa $t_{in}$: temperature of inlet gas, ° C.

h: relative humidity of inlet gas, %

The foregoing calculation may also be done by using a computer software package for analysis, for example, BIO-STAR, commercially available as a software package for real-time analyzing data of a fermentation process.

In a specific embodiment, the comparison of Step (b) also includes the following steps:

(i) comparing the physiological metabolic parameters and the characteristics associated with the physiological metabolic parameters as measured in step (a) with the physiological metabolic parameters, the characteristics associated with the physiological metabolic parameters or combinations thereof having predetermined values;

(ii) adjusting the physiological metabolic parameters, the characteristics associated with the physiological metabolic parameters or combinations thereof of the biochemical reactor to make the difference between the physiological metabolic parameters of the biochemical reactor and those having predetermined values is no more than 10%-15%, and choosing a biochemical reactor bearing measurements closest to the predetermined values;

(iii) determining a reactor that is optimized and scaled-up accordingly.

In a preferred embodiment, in the adjustment of Step (ii), the physiological metabolic parameters, the characteristics associated with the physiological metabolic parameters or combinations thereof are adjusted as follows to control the fermentation process: adjusting the relationship between oxygen uptake rate and dissolved oxygen concentration, revolution speed or air flow rate and dissolved oxygen concentration, supplementing sugar and pH, supplementing sugar and carbon dioxide evolution rate, carbon dioxide evolution rate and biomass, carbon dioxide evolution rate and pH, carbon dioxide evolution rate and oxygen consumption rate, and gas flow rate and pH.

In a preferred embodiment, the method gains control over the fermentation process by way of detecting temperature, agitation speed, gas flow rate, tank pressure, defoaming, pH, dissolved oxygen concentration, real volume and weight of a fermentation broth, amount of supplement (including substrate, precursor, oil, and acidic/basic substance), exhaust gas $CO_2$ and exhaust gas $O_2$, and adjusting the relationship between oxygen uptake rate and dissolved oxygen concentration, revolution speed or flow rate and dissolved oxygen concentration, supplementing sugar and pH, supplementing sugar and carbon dioxide evolution rate, carbon dioxide evolution rate and cell amount, carbon dioxide evolution rate and pH, carbon dioxide evolution rate and oxygen consumption rate, and gas flow rate and pH.

In a preferred embodiment, the predetermined values in Step (b) are those of the physiological metabolic parameters, the characteristics associated with the physiological metabolic parameters or combinations thereof of a small fermenter, wherein the biochemical reactor is no less than 20-2000 times the volume of the small fermenter.

In a preferred embodiment, the volume of the small fermenter is, for example, 5, 10, 20, 30, 50, 100 L.

In the fourth aspect of the invention, the use of the biochemical reactor of the invention in optimizing and scaling up a fermentation process is provided.

In a preferred embodiment, the use is to optimize and scale up the fermentation process of vitamin $B_{12}$ or cephalothin.

The beneficial effects of the invention include:

(1) The parallel light beams emitted by a light source in the in-situ cell examination microscope of the biochemical reactor, are transformed by the replaceable color filter into beams in a particular wave band, and further transformed by the annular diaphragm plate into annular parallel beams. Illumination beams with a large annular aperture angle are obtained through the reflector and illuminate the cell culture in the sampling pool between the sampling piece and the observation window. Since the illumination beams are directed in around the cell culture, a majority of them will not be reflected back to the object lens. Thus, the visual field is a dark one. Only those beams reflected by the illuminated cells or particles in the culture pass the object lens and are reflected again by a 45° reflecting prism coated with a reflective film to a CCD image sensor or an area array image sensor. Therefore, the wavelength of the exterior light system of the invention can be changed conveniently by replacing the color filter, and the dark field may help improve the contrast and the resolution of the image of a transparent cell obtained by the microscope which thus may be used to observe the morphology of a bacterium, a fungus or an animal cell dynamically during a bioprocess, distinguish dead cells from living ones, and enable morphological analysis so as to provide guidance for optimizing a fermentation process. In addition, since the sampling device of the in-situ cell examination microscope of the reactor consists of a sampling piece, a flexible element and a movable device, and a sampling pool between the end face of the sampling piece and the observation window of the in-situ cell examination microscope is formed, the cells in the sampling pool, which is isolated from the biochemical reactor, are separated from the cells in the biochemical reactor. Thus, the cells in the sampling pool are not driven to move by the agitator in the biochemical reactor, leading to easier observation thereof.

(2) The biochemical reactor with an in-situ cell examination microscope is characterised in the simple structure, easy use, low cost, and the like.

(3) Along with the development of modern molecular biology in 20th century, the research on biology has advanced from macro field to micro field, from the description of morphology and phenotype to the interpretation of various molecules and their functions in an organism, further to the comprehension of all possible interrelations of all genes, proteins and components of metabolic products. Therefore, the mechanism of intracellular processes is getting more and more clear. However, the research focused merely on physiological regulation mechanism can usually reveal just a local aspect or a temporary feature of physiological regulation. Highly branched and dispersed research can not play a decisive role in controlling, optimizing and scaling up the whole process of a biochemical reactor. Thus, it is a fundamental task of great importance to combine biology and engineering science to cope with the relationships between part and whole, dynamic states and final results, strain breeding and process optimization. It is attempted in the present invention to resolve the above systematic problems using engineering processes based on the research on the multi-scale problems in a biochemical reactor. Various parameters obtained according to the invention and the analysis methods and the relevant softwares put forward in the invention may be used to reduce a complex biological process in a biochemical reactor into characteristics of various scales, so as to study the relations between events of different scales, their changes from quantity to quality, and the effects thereof on the whole complex system. This provides a basis for coping with the relationship between part and whole during optimizing and scaling-up a fermentation process.

(4) In a preferred embodiment, in addition to conventional measurements and sensors, the living cell sensor and the in-situ cell examination microscope are important tools for metabolic regulation analysis involving the fermentation process and cell growth. The living cell sensor may effect real-time monitoring of cell growth and overcome the difficulty in distinguishing particles in a composite culture medium, dead cells and living cells. This makes it possible to carry out precise study on primary and secondary metabolic regulation in the fermentation process, element balance in the fermentation process, metabolic engineering, isotope analysis, and the like. Since the illumination beams emitted by the light source in the in-situ microscope are directed in around the cell culture and do not return to the object lens, the visual field is a dark one. The dark field improves the contrast and the resolution of the image of a transparent cell obtained by the microscope which thus may be used to observe the morphology of a bacterium, a fungus or an animal cell dynamically during a bioprocess, distinguish dead cells from living ones, and help make morphological analysis so as to provide guidance for optimizing a fermentation process.

(5) In a preferred embodiment, a computer is used to process relevant data, so as to correlate the change of cell morphology with all detected parameters instantly and dynamically. This provides an important basis for multi-scale parameter analysis of a fermentation process.

BRIEF DESCRIPTION OF THE DRAWINGS

FIG. 4a-4c are the schematic views of the structures of various specific embodiments of the biochemical reactor according to the invention, wherein FIG. 4a is the schematic view of the arrangements of the control parameters of the biochemical reactor; FIG. 4b is the schematic view of the pipeline system of the biochemical reactor; and FIG. 4c is the schematic view of the tank body.

FIGS. 10a-10h show the results of optimization and scale-up of a cephalosporin C fermentation process using the biochemical reactor according to the invention, wherein:

FIG. 10a shows the characteristic relationship between DO and OUR in the fermentation process according to Example 3.

FIG. 10b shows the parameter changes resulted from the shift of carbon sources utilization according to Example 3.

FIG. 10c shows the change tendencies of real time physiological parameters between lab scale and industrial scale fermenters according to Example 3.

FIG. 10d shows the profiles of pH and RQ from lab scale fermenter and industrial fermenter according to Example 3.

FIG. 10e shows the simulated flow field in a vertical plane of 160 m$^3$ fermenter according to Example 3 (gas flow rate A: 0.5 vvm, B: 1.2 vvm).

FIG. 10f shows the simulated air volume distribution in a vertical plane of 160 m$^3$ fermenter according to Example 3 (gas flow rate A: 0.5 vvm, B: 1.2 vvm).

FIG. 10g shows the impeller combinations and simulated air volume distribution in a vertical plane of 160 m$^3$ fermenter after alteration according to Example 3.

FIG. 10h shows the process parameters of cephalosporin fermentation before and after the change of the impeller lengths (F: before; L: after) according to Example 3.

FIGS. 11a-11e show the results of optimization and scale-up of a VB$_{12}$ fermentation process using the biochemical reactor according to the invention, wherein:

FIG. 11a is the process parameters of VB$_{12}$ fermentation in 9 m$^3$ fermentor according to Example 4.

FIG. 11b is the process parameters of VB$_{12}$ fermentation in low dissolved oxygen concentration according to Example 4.

FIG. 11c is the process parameters of VB$_{12}$ fermentation in high dissolved oxygen concentration according to Example 4.

FIG. 11d is the time profiles of total sugar, NH$_2$—N, cell growth and VB$_{12}$ production in two DOC control levels according to Example 4.

FIG. 11e is the time profiles of specific growth rate ($\mu$) and specific production rate ($q_p$) of VB$_{12}$ fermentation in two DOC control levels according to Example 4.

THE PREFERRED EMBODIMENTS FOR CARRYING OUT THE INVENTION

The invention will be described in more detail with reference to the drawings and examples.

Example 1

The invention provides a biochemical reactor with an in-situ microscope, wherein the in-situ microscope 4 is arranged in the biochemical reactor 41.

Figure 5:
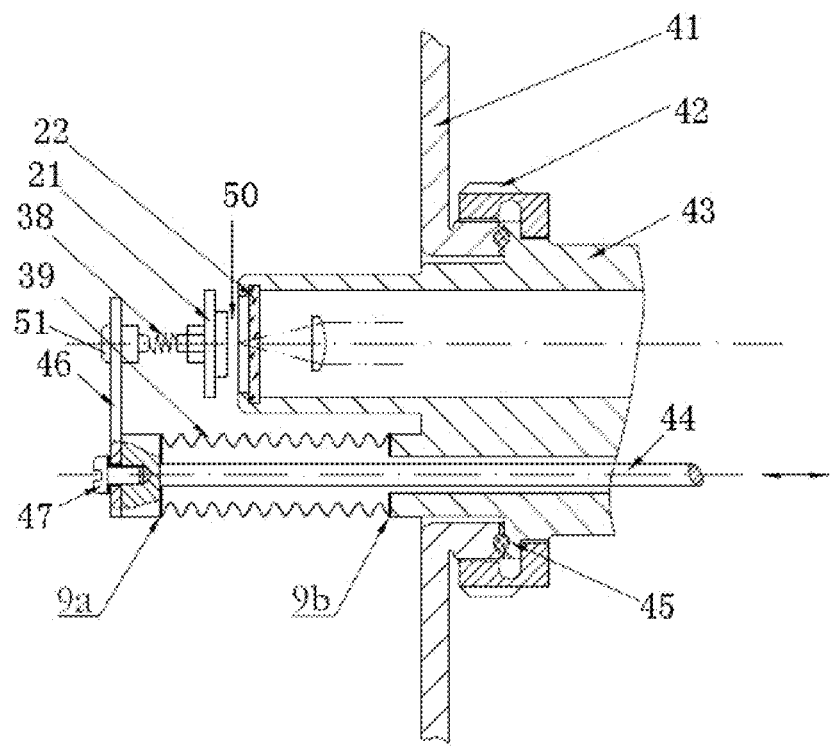
FIG. 5 is the schematic view of the structure of a specific embodiment of the biochemical reactor according to the invention.
Figure 6:
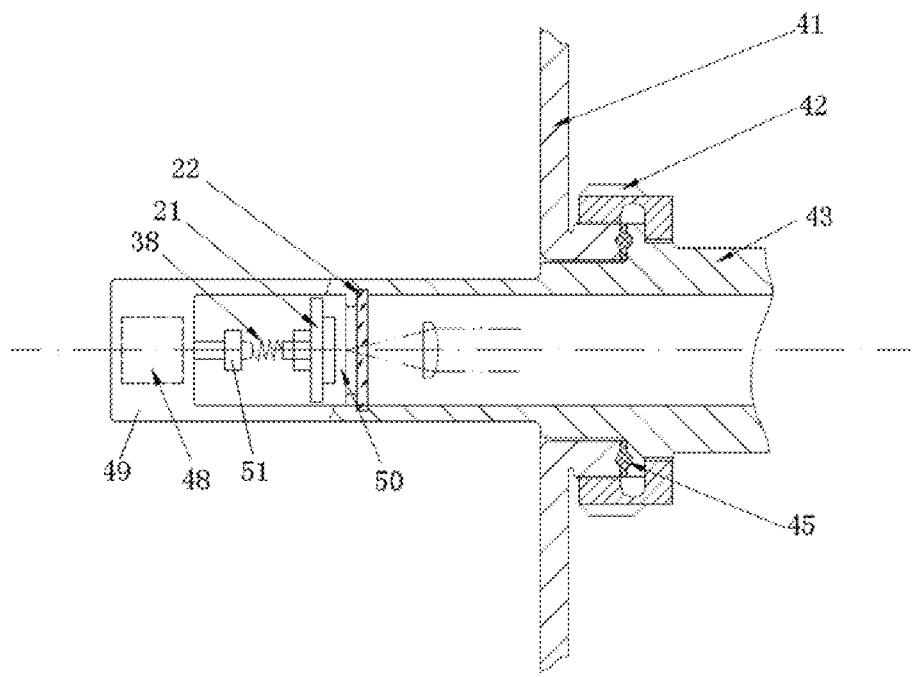
FIG. 6 is the schematic view of the structure of another specific embodiment of the biochemical reactor according to the invention.

As shown in FIGS. 5 and 6, the main body 43 of the in-situ cell examination microscope is connected to the biochemical reactor 41 via a locknut 42, and the interface between the main body 43 of the in-situ cell examination microscope and the biochemical reactor 41 is sealed via a gasket 45.

The biochemical reactor 41 includes but is not limited to a microbe reactor, an animal cell reactor and a photo-biological reactor.

There is no specific limitation to the position where the in-situ cell examination microscope 4 is installed in the biochemical reactor as long as the subject to be observed in biochemical reactor can be observed. For example, it can be installed in a conventional manner at a desired position in the biochemical reactor, more specifically, for example, at a position on the reactor wall at 36%-70% height relative to the total volume of the reactor.

The in-situ cell examination microscope of the invention may be used to observe the growth and the morphology change of the cells in the biochemical reactor, more specifically to count the number of the cells.

A conventional agitator in the art may also be arranged in the biochemical reactor of the invention. There is no specific limitation to the agitator as long as the system in the biochemical reactor can be mixed desirably.

The biochemical reactor of the invention may further include conventional detecting devices, for example, one or more of a pH sensor, a DO (dissolved oxygen) sensor and a temperature sensor. There is no specific limitation to the detecting devices as long as the parameters of the system in the biochemical reactor can be measured as desired.

As shown in FIGS. 5 and 6, the sampling device 40 consists of a sampling piece 21, a flexible element 38 and a movable device, wherein the sampling piece 21 and the driving axle 51 of the movable device are connected by the flexible element 38, and the space between the front end face of the sampling piece 21 and the observation entrance window 22 forms a sampling pool 50.

As shown in FIG. 5, one form of the movable device consists of a driving axle 51, a connecting rod 46, a pulling rod 44 for sampling and a flexible element 39, wherein the connecting rod 46 equipped with the driving axle 51 is connected to the pulling rod 44 for sampling through a screw 47, the pulling rod 44 for sampling and the flexible element 39 are welded together at a position 9a to give a sealed joint, and the other end face of the flexible element 39 is connected to the main body 43 of the microscope at a position 9b also by welding.

The observation entrance window 22, made from stainless steel or sapphire, of the microscope is positioned within the biochemical reactor 41. The sampling piece 21, also made from stainless steel or sapphire, consists of three cylinders of different diameters. One end face of the sampling piece 21 is welded together with the flexible element 38, while the other end face could move along the central axis of the observation window of the microscope from side to side, and forms a sampling pool 50 with the observation window 22 of the microscope.

When the pulling rod 44 for sampling is pulled outward, the pulling rod 44 for sampling pushes the sampling piece 21 toward the observation window 22 via the connecting rod 46 and the flexible element 38, while the flexible element 39 is compressed. When the pulling rod 44 for sampling is pushed inward, the pulling rod 44 for sampling pushes the sampling piece 21 away from the observation window 22 via the connecting rod 46 and the flexible element 38, while the flexible element 39 is relaxed. The flexible element 38, the flexible element 39, the connecting rod 46 and the pulling rod 44 are all made from stainless steel.

Figure 7:
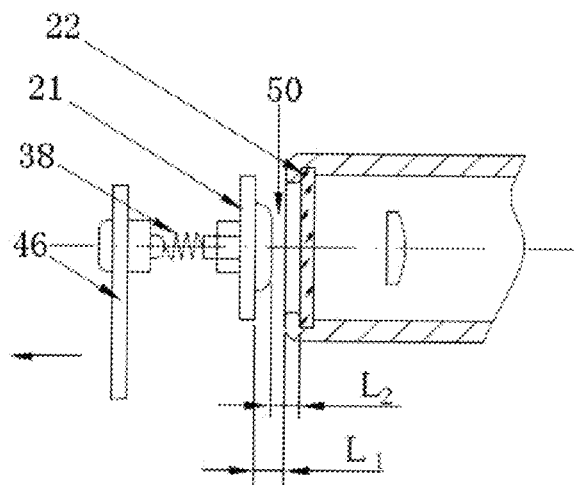
FIGS. 7 and 8 are the schematic views showing the operation of a sampling pool of an in-situ microscope in the biochemical reactor.
Figure 8:
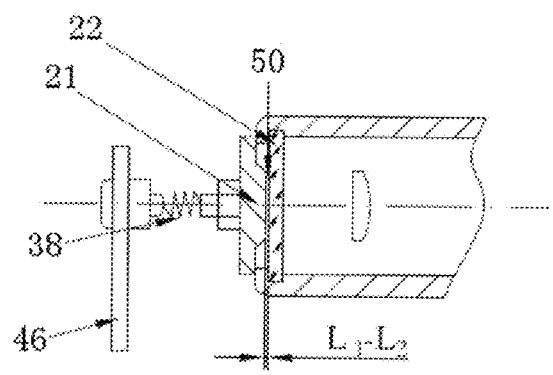

As shown in FIGS. 7 and 8, when the connecting rod 46 moves as directed by the arrow, the connecting rod 46 brings the sampling piece 21 via the flexible element 38 to move away from the observation window 22, and thus the distance between the sampling piece 21 and the observation window 22 gets larger. In such a case, the sampling pool 50 formed between the sampling piece 21 and the observation window 22 is in connection with the biochemical reactor 41, so that the cell culture in the sampling pool is in fluid connection with that in the biochemical reactor. When the connecting rod 46 brings the sampling piece 21 via the flexible element 38 to move toward the observation window 22, the distance between the sampling piece 21 and the observation window 22 gets smaller. When the distance can no longer get smaller, the space between the end face of the sampling piece 21 and the observation window 22 forms a sampling pool 50 that is isolated from the biochemical reactor 41. In such a case, the cell culture in the sampling pool 50 is isolated from that in the biochemical reactor and can not be driven to move by the agitator in the biochemical reactor, leading to easier observation thereof. The depth of a formed sampling pool may be adjusted by controlling the distance between the end face of the sampling piece 21 and the observation window 22.

As shown in FIG. 6, another form of the movable device consists of a driving axle 51, an electric motor 48 and a sampling tube 49, wherein the sampling tube 49 is connected to the front end of the main body 43 of the microscope, the electric motor 48 is arranged at the back of the sampling tube 49, and the output axle of the electric motor 48 is connected to the driving axle 51.

The main body 43 of the microscope is connected to the biochemical reactor 41 via a locknut 42. The sampling pool 50 is formed by the space between the end face of the sampling piece 21 and the observation window 22. The electric motor 48, which is high-temperature resistant, is sealed in the main body 43 of the microscope at the part which is submerged in the culture in the biochemical reactor. When the electric motor 48 brings the sampling piece 21 via the flexible element 38 to a limit position in a direction which makes the volume of the sampling pool 50 get smaller, the cell culture in the sampling pool 50 is isolated from that in the biochemical reactor 41, and thus the cell culture in the sampling pool is relatively static, leading to easier observation thereof. Contrarily, when the electric motor 48 brings the sampling piece 21 to move in the opposite direction, the cell culture in the sampling pool 50 and that in the biochemical reactor 41 mix together.

Figure 9:
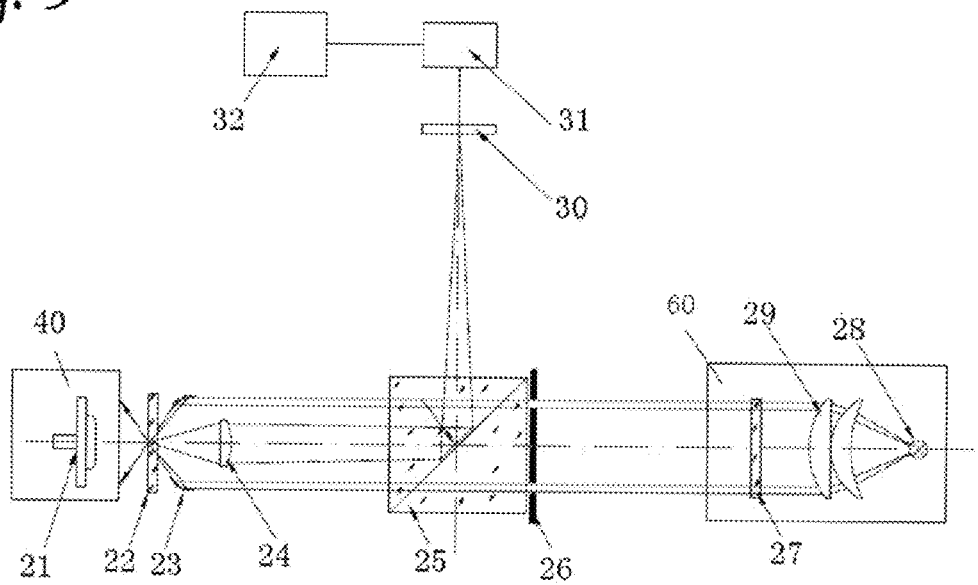
FIG. 9 is the schematic view showing the illumination and imaging of an in-situ microscope in the biochemical reactor.

As shown in FIG. 9, the in-situ microscope in the biochemical reactor of the invention comprises a main body 43 of the microscope, a reflector 23, an object lens 24, an observation entrance window 22, a sampling device 40, an exterior light source system 60, a reflecting prism 25, an annular diaphragm plate 26 and a CCD or an area array image sensor 30.

The observation entrance window 22 is arranged in the front of the main body of the microscope. The sampling device 40 is arranged in front of the observation entrance window 22. In the main body 43 of the microscope, both of the object lens 24 and the exterior light source system 60 are arranged behind the observation entrance window 22.

The reflecting prism 25 is arranged between the exterior light source system 60 and the object lens 24. The reflector 23 is arranged behind the object lens 24 while in front of the observation entrance window 22. The annular diaphragm plate 26 is arranged in front of the reflecting prism 25. The CCD or the area array image sensor 30 is arranged above one side of the reflecting prism 25.

The exterior light source system 60 consists of a light source 28, a condenser 29 and a replaceable color filter 27, wherein the light source 28 may be a halogen lamp or a LED lamp, and the light beams emitted by the lamp are focused by the condenser 29 to give parallel beams. After the parallel light beams are transformed by the replaceable color filter 27 into beams in a particular wave band, the beams are further transformed by the annular diaphragm plate 26 into annular parallel beams. Illumination beams with a large annular aperture angle are obtained through the reflector 23 and illuminate the cell culture in the sampling pool between the sampling piece 21 and the observation window 22. Since the illumination beams are directed in around the cell culture, a majority of them will not be reflected back to the object lens 24. Thus, the visual field is a dark one. Only those beams reflected by the illuminated cells or particles in the culture pass the object lens 24 and are reflected again by the 45° reflecting prism 25 coated with a reflective film to the CCD image sensor or an area array image sensor 30. After photoelectric conversion in the CCD or the area array image sensor 30, the resulting digital signals are sent to an image acquisition and processing unit 31, which then sends the processing results to a computer for analysis, display or store.

Figure 1:
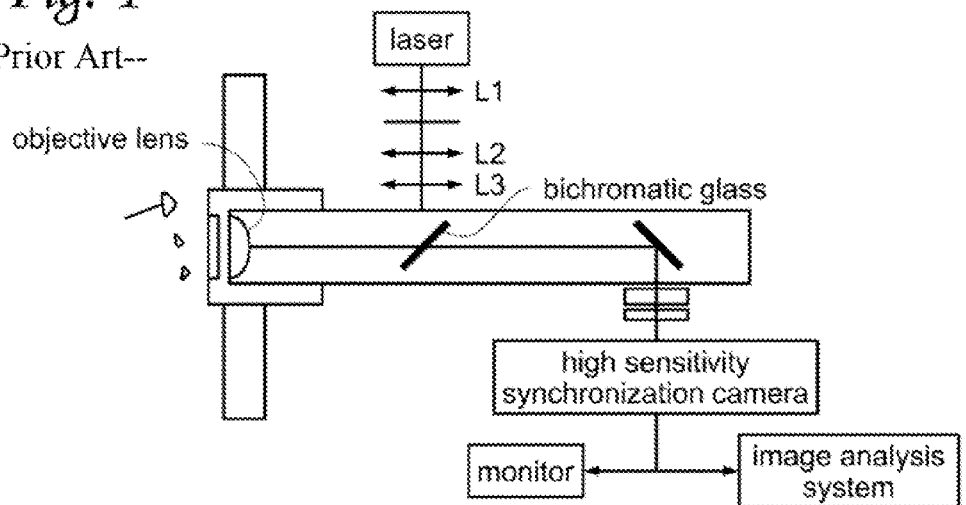
FIG. 1 shows the structure and the working principle of an in-situ microscope based on fluorescence-excitation process.
Figure 2:
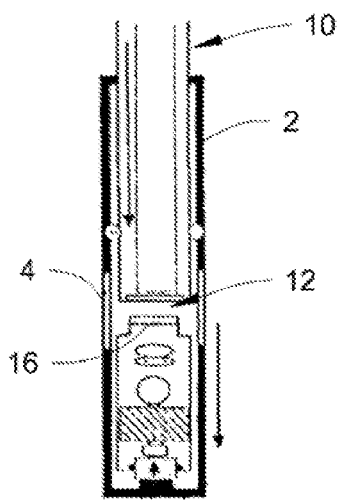
FIG. 2 shows the optical principle of a microscope according to U.S. Pat. No. 6,809,862.
Figure 3:
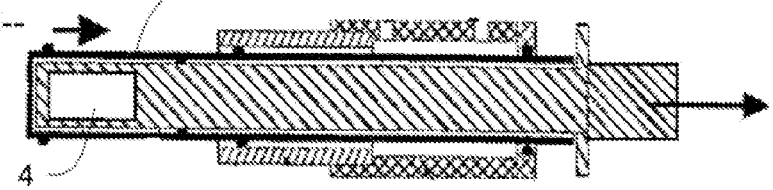
FIG. 3 is the schematic views of the structures of the sampling chamber and the rinsing chamber of a microscope according to U.S. Pat. No. 6,809,862.
Figure 3:
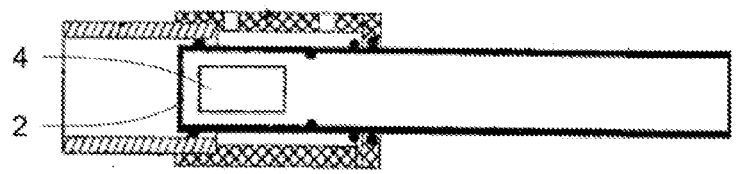
Figure 4A:
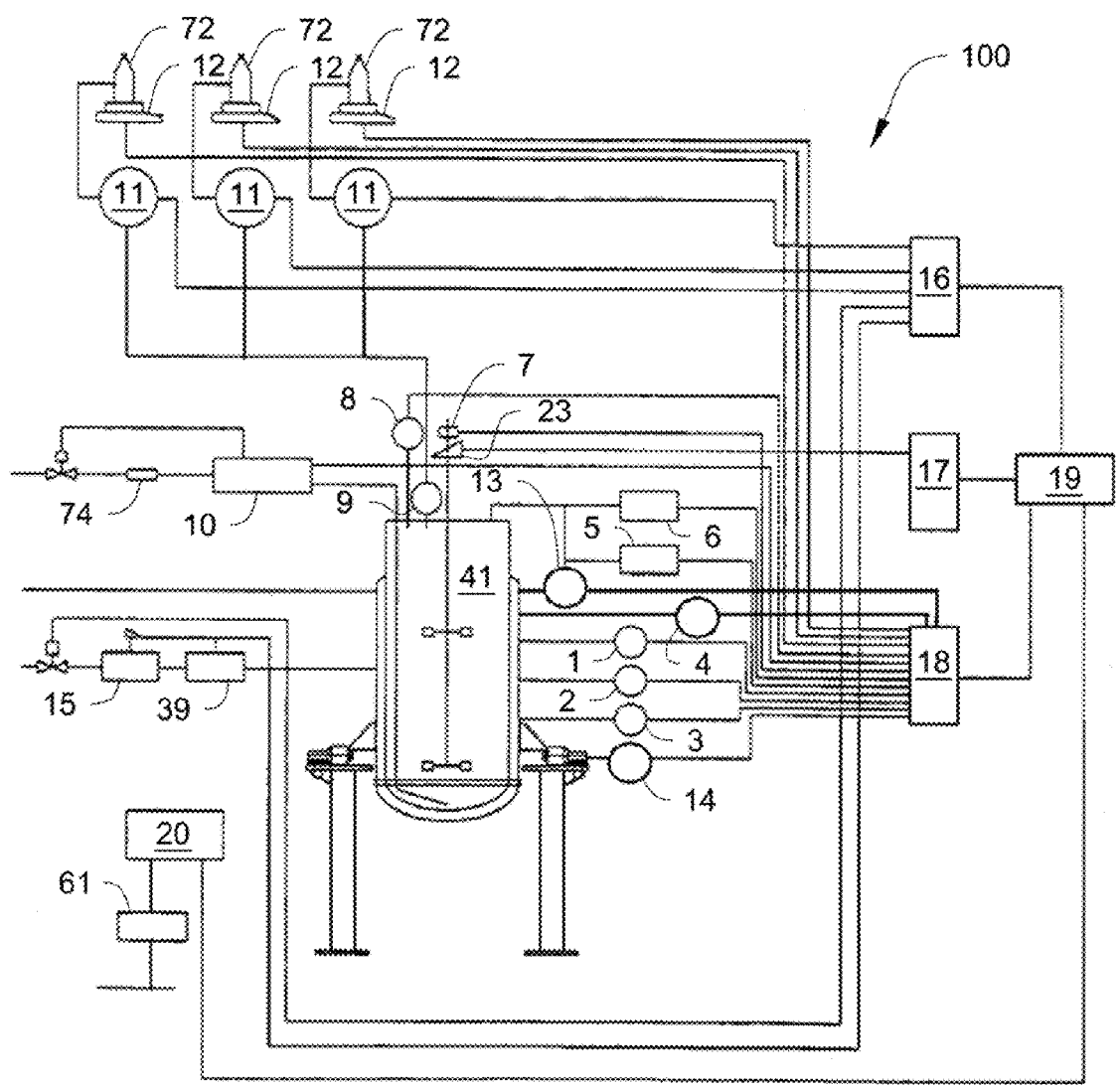

As shown in FIG. 4a, in a specific embodiment of the invention, a living cell sensor 13 is further arranged on the body of the biochemical reactor. The living cell sensor 13 may be any conventional living cell sensor in the art. Preferably, The living cell sensor 13 is a living cell sensor using a four-electrode system. When a four-electrode system is used in the living cell sensor 13, the protoplast in a living cell acts as electrolyte when the cell is placed in an alternating electric field, and the capacitance resulting from the polarization of the alternating electric field correlates with the biomass. Since different polarizing effects will result from the change of the frequency of the alternating electric field, this can be used to determine the optimal measuring conditions. The capacitance measured as the corresponding signal is sent to a computer for data processing, as the base of the biomass for multi-parameter correlation analysis.

Figure 4B:
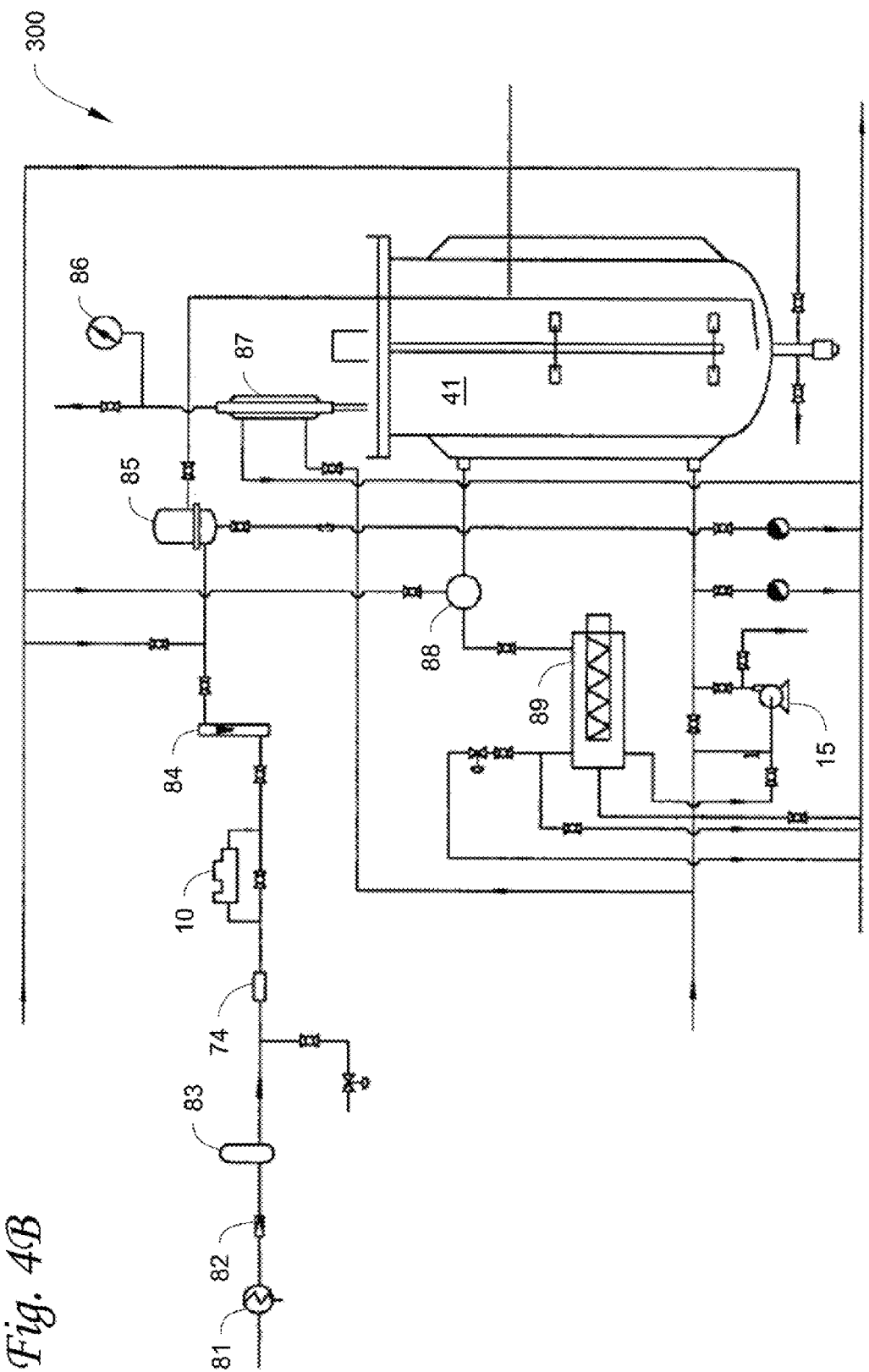
Figure 4C:
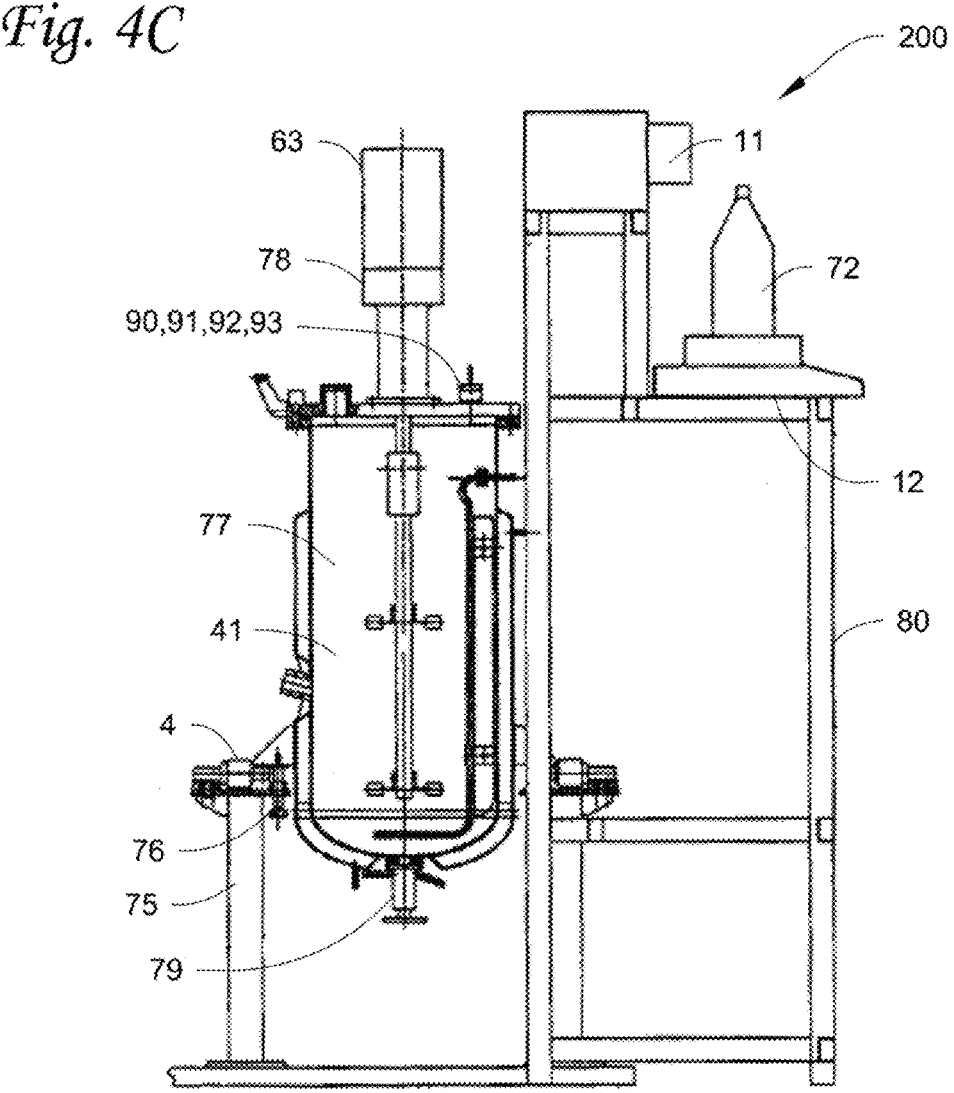
Figure 4C:
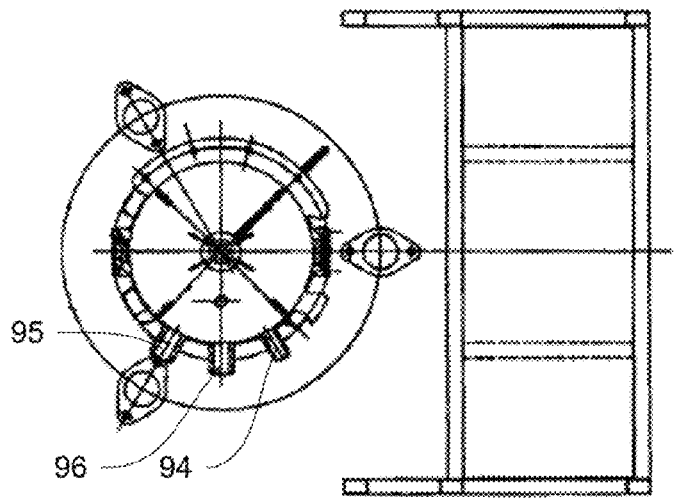

As shown in FIG. 4a-4c, the following components for process optimization and data scale-up are further arranged on the body of the biochemical reactor 41: a sensing system 100 with apparatuses, instruments and sensors for detecting and controlling multiple parameters (FIG. 4a), a process pipeline system 200 with installing supports (FIG. 4c), and an electric control cabinet 300 with industrial personal computers and executing components (FIG. 4b).

As shown in FIG. 4a, the sensing system 100 with apparatuses, instruments and sensors for detecting and controlling multiple parameters comprises a temperature sensor 1, a pH sensor 2, a dissolved oxygen sensor 3, a whole-tank weight sensor 14, an exhaust gas $CO_2$ interface 5, an exhaust gas $O_2$ interface 6, a speed sensor 7, a pressure sensor 8, a defoaming sensor 9, a living cell sensor 13 and an in-situ microscope 4, wherein the multiple parameters include temperature, agitation speed, gas flow rate, tank pressure, defoaming, pH, dissolved oxygen concentration, real volume and weight of fermentation broth, amount of the supplement (including substrate, precursor, oil, and acidic/basic substance), exhaust gas $CO_2$ and exhaust gas $O_2$, amount of living cells, and parameters of the in-situ microscope.

As shown in FIG. 4c, the process pipeline system 200 with installing supports arranged on the body of the biochemical reactor 41 comprises a feed flask 72, a preheater 74, a stand 75 for whole-tank weighing, a special support 76 for sampling, a tank body assembly 77, a quick detachable bedplate 78, an electric motor 79, a pipe rack 80, an oil-water separator 81, a pressure reducing valve 82, a filter 83, a flow meter 84, an air filter 85, a pressure gauge 86, a cooler 87, a pipe sight glass 88, a water heater 89, a sampling valve 90 with no dead volume, a defoaming sensor interface 91, an exhaust gas $CO_2$ interface 92, an exhaust gas $O_2$ interface 93, a temperature sensor 94, a pH sensor interface 95 and a DO sensor interface 96. A sensing system 100 is also arranged on the biochemical reactor 41 (not shown).

As shown in FIG. 4b, the electric control cabinet 300 with industrial personal computers and executing components comprises a thermal mass flow meter 10, a high-precision peristaltic pump 11, a supplement weighing sensor 12 (an electronic balance for supplementing substrate, an electronic balance for a precursor or oil, an electronic balance for acidic/basic substance), a circulating pump 15, an electromagnetic valve 16, a digital-to-analog converter 17, a analog-to-digital converter 18, a local computer 19, an upper computer 20, a modem 61 and a rare-earth motor 63. A sensing system 100 is also arranged on the biochemical reactor 41 (not shown).

In a preferred embodiment, computer softwares are used in the electric control cabinet with industrial personal computers and executing components to effect in-situ acquisition of parameters, off-line computation of parameters, data recording and in-situ control of part of parameters according to the need of field data acquisition and handling as well as the requirement of process optimization, and to send all data concerning the parameters synchronously to the upper computer via a local area network, wherein the upper and local computers are programmed using configuration language and C language, and simple redundancy technology is used in data recording.

Example 2

2.1 Observation of the Fermentation Process of Recombinant Yeast

To verify the invention, an in-situ cell examination microscope for a biochemical reactor as described in Example 1 was used in a biochemical reactor to observe the fermentation process of recombinant yeast (available from INVITRO Co.).

During the culture, the fermentation broth was sampled every 2 hours, cell optical density (OD600) and cell dry weight were measured, and the number of cells was counted using an off-line hematocyte counter every 2 hours. Meanwhile, the in-situ cell examination microscope was used to make automatic observation and counting. The results were shown in Table 1.

As indicated by Table 1, the numbers of cells obtained using the in-situ cell examination microscope were essentially consistent with those obtained using the off-line hematocyte counter, although the results at the later stage during the culture showed some difference. When cell concentrations were fitted with fermentation time using exponent equation, the linear correlation coefficient resulting from those data obtained using the in-situ cell examination microscope was the highest and essentially consistent with that resulting from those data obtained using the off-line hematocyte counter, but significantly higher than those resulting from cell optical density and cell dry weight. An explanation for this is the incapability of the optical density process and the dry weight process to distinguish dead cells, living cells and solid particles in the fermentation broth, leading to rather great errors.

TABLE 1

Comparison of Off-line Cell Count, In-situ Cell Count, Cell Optical Density and Cell Dry Weight

| Culture Time (h) | Cell Number Obtained by Off-line Hematocyte Counter ($10^7$/mL) | Cell Number Obtained by In-situ Cell examination Microscope ($10^7$/mL) | Cell Optical Density OD600 | Cell Dry Weight DCW(g/L) |
|---|---|---|---|---|
| 0 | 0.99 ± 0.12 | 1.2 ± 0.08 | 8.2 | 6.1 |
| 4 | 3.10 ± 0.11 | 3.12 ± 0.09 | 8.9 | 6.6 |
| 6 | 6.29 ± 0.10 | 6.31 ± 0.10 | 10.1 | 7.2 |
| 8 | 12.11 ± 0.11 | 12.27 ± 0.10 | 12.1 | 8.3 |
| 10 | 16.46 ± 0.09 | 16.50 ± 0.11 | 13.8 | 9.2 |
| R2(Linear Correlation) | 0.9908 | 0.9934 | 0.9237 | 0.9353 |

2.2 Observation of the Fermentation Process of Recombinant Animal Cells

To verify the invention, an in-situ cell examination microscope for a biochemical reactor as described in Example 1 was used in a biochemical reactor to observe the fermentation process of recombinant animal cells (HEK 293, available from Shanghai Institute of Biochemistry and Cell Biology).

During the culture, the fermentation broth was sampled every 24 hours and the number of cells was counted using an off-line hematocyte counter. Meanwhile, the in-situ cell examination microscope was used to make automatic observation and counting. The results were shown in Table 2. As indicated by Table 2, the cell numbers obtained using the in-situ cell examination microscope were essentially consistent with those obtained using the off-line hematocyte counter.

TABLE 2

Cell Density of HEK293 in a Reactor with Mechanical Agitation

| Time | day 0 | day 1 | day 2 | day 3 | day 4 | day 5 | day 6 |
|---|---|---|---|---|---|---|---|
| Hematocyte Counter ($\times 10^5$ cells/mL) | 1.50 ± 0.2 | 2.5 ± 0.2 | 3.6 ± 0.2 | 5.0 ± 0.2 | 6.8 ± 0.2 | 9.0 ± 0.2 | 7.2 ± 0.2 |
| In-situ Count($\times 10^5$ cells/mL) | 1.48 ± 0.2 | 2.3 ± 0.2 | 3.5 ± 0.2 | 4.9 ± 0.2 | 6.9 ± 0.2 | 8.8 ± 0.2 | 7.1 ± 0.2 |

Example 3

1. Materials and Methods 1.1 Experimental Strains

*Cephalosporium Acremonium* AC0508 (available from Shanxi Weiqida Pharmaceuticals Co.)

1.2 Culture Media 1.2.1 Shake-Flask Culture

Slope culture medium (100 mL): 1.2 g wort, 1.2 g peptone, 2.2 g agar, pH 7.0 (before sterilization)

Seed culture medium (100 mL): 3.0 g corn steep liquor, 0.4 g ammonium acetate, 2 g sucrose, 0.02 g DL-methionine, 0.05 g $CaCO_3$, pH 6.5 (before sterilization)

Fermentation culture medium (100 mL): 7 g corn steep liquor, 4 g starch, 0.03 g amylase, 1 g soybean oil, 0.2 g DL-methionine, 0.4 g $KH_2PO_4$, 0.8 g $(NH_4)_2SO_4$, 0.005 g $FeSO_4 \cdot 7H_2O$, 1 g $CaCO_3$, pH 6.2 (before sterilization)

1.2.2 Fermenter Culture

Primary seed culture medium (100 L): 1 kg glucose, 2.5 kg sucrose, 1 kg corn steep liquor, 3 kg soybean cake powder, 0.5 g $CaCO_3$, 0.08 kg defoamer, pH 6.0 (before sterilization)

Secondary seed culture medium (100 L): 1 kg glucose, 5 kg sucrose, 3 kg corn steep liquor, 5 kg soybean cake powder, 1 kg peanut cake powder, 0.5 kg $CaCO_3$, 0.05 kg defoamer, pH 6.0 (before sterilization)

Fermentation culture medium (100 L): 5.0 kg dextrin, 5.0 kg soybean oil, 3 kg corn steep liquor, 3 kg soybean cake powder, 2 kg peanut cake powder, 0.5 kg methionine, 1.2 kg ammonium sulfate, 1.0 kg potassium sulfate, several other microelements, 0.8 kg $CaCO_3$, 0.048 kg defoamer, pH 6.0 (before sterilization)

1.3 Culture Methods 1.3.1 Shake-Flask Fermentation

*Cephalosporium Acremonium* was inoculated into the seed culture medium from a test tube slant, and placed on a rotary shaker (eccentric distance: 5 cm, speed: 220 r/min) to culture at 28° C. for 88 hours. Then, it was inoculated into a fermenter with an inoculalum amount of 20% to culture at 28° C. After 40 hours, the temperature was kept at 25° C. to culture for another 29 hours before harvesting.

1.3.2 Fermenter Operation

Primary seed tank process control: inoculum amount 0.25%, tank temperature 30° C., air ratio 1:2 (VVM), culture time ~72 hours, pH≥7.5. When PMV>20%, the culture was transferred.

Secondary seed tank process control: inoculum amount 4.0%, tank temperature 30° C., air ratio 1:0.6 (VVM)-1:2.0 (VVM), culture time ~60 hours, pH≥7.5. When PMV>25%, the culture was transferred.

Fermenter process control: inoculum amount 20.0%; tank temperature 30° C. for the first 30 hours, 25° C. for another 80 hours, 24° C. until discharge of the tank content; air ratio 1:0.8 (VVM)-1:1.2.0 (VVM). Soybean oil was supplemented after 70 hours. When pH<5.5, ~20% aqueous ammonia was added automatically under the control of a computer to maintain the culture at pH 5.5.

1.4 Instruments and Analysis Methods

This experiment was first carried out on a full-automatic laboratory fermenter with multi-parameter monitoring function FUS-50L(A) (available from Shanghai GuoQiang BioEngineering Equipments Co., Ltd). It was also carried out on an industrial scale fermenter modified correspondingly and equipped with BIOSTAR software package (available from East China University of Science and Technology), and the parameters monitored were the same as those obtained from the above laboratory fermenter. In addition to conventional devices for measuring and controlling pH, DO, temperature, revolution speed and the like, the laboratory fermenter system and the industrial scale fermenter system were equipped with exhaust gases $O_2$ and $CO_2$ analyzers. Both systems were able to monitor in-situ and control 10 or more (more specifically, 14) parameters, including the amount of living cells obtained particularly using an in-situ cell examination microscope. They were also provided with software packages BIORADAR and BIOSTAR, into which parameters obtained by manual measurement in a laboratory could be input, so that precise indirect parameters, which were necessary for optimization and scale-up of a fermentation process and included various metabolic flux characteristics or engineering features, for example, carbon dioxide evolution rate (CER), respiratory quotient (RQ), volume oxygen transfer coefficient (KLa) and the like, were further obtained.

Among the parameters obtained using BIORADAR and BIOSTAR, oxygen OUR was calculated through the following equation:

$$OUR = \frac{F_{in}}{V}\left[C_{O_2 in} - \frac{C_{in.in} \cdot C_{O_2 in}}{1 - (C_{O_2 out} + C_{CO_2 out})}\right] \cdot f$$

wherein:
$F_{in}$: inlet gas flow, (mol)
$C_{in.in} \backslash C_{O2.in} \backslash C_{CO2.in}$: concentrations of inert gas, oxygen and carbon dioxide in the inlet gas, respectively, % (V)
$C_{O2.out} \backslash C_{CO2.out}$: concentrations of oxygen and carbon dioxide in the outlet gas, respectively, % (V)
V: volume of the fermentation broth, (L)
f is calculated through the following equation:

$$f = \frac{273}{273 + t_{in}} \cdot P_{in} \cdot \frac{1}{1+h} \times 10^{-5}$$

wherein:
$P_{in}$: absolute pressure of inlet gas, Pa
$t_{in}$: temperature of inlet gas, °C.
h: relative humidity of inlet gas, %

HPLC method for measuring concentrations of cephalosporin C: HP 1100 chromatographic system; chromatographic column: TSKgel ODS-100S 4.6×250 mm, 10 μm; mobile phase: 20 mM buffer solution of ammonium acetate (pH 5.6): acetonitrile=94:6; flow rate: 1.0 ml/min; UV wavelength: 254 nm; temperature: room temperature; sample volume: 20 μl.

PMV method for measuring cell concentrations: 10 ml fermentation broth was sampled and centrifuged for 20 minutes at 3000 r/min.

2. Results and Analysis 2.1 Change of Parameters Resulting from High Oxygen Consumption Process during the Fermentation of Cephalosporin C Firstly, the metabolic characteristics of *Cephalosporium Acremonium* was studied in a 50 L laboratory fermenter, and plots of the metabolic characteristics relevant to high oxygen consumption of *Cephalosporium Acremonium* was obtained as shown in FIG. 10a.

Figure 10A:
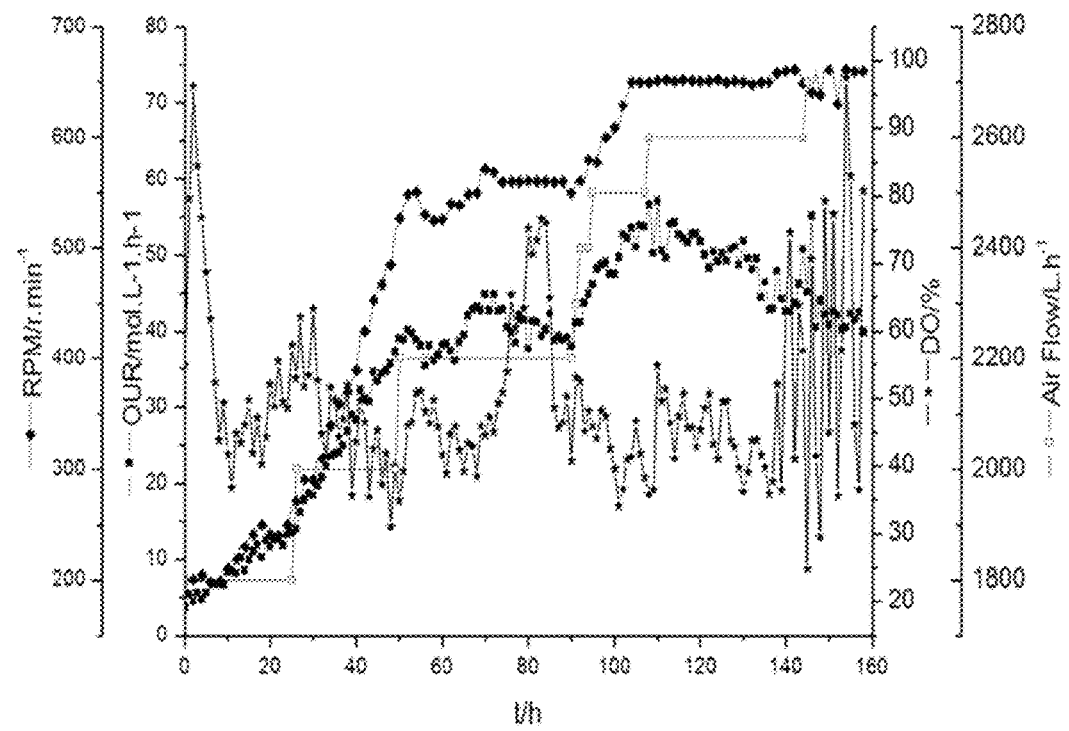
Figure 10A:
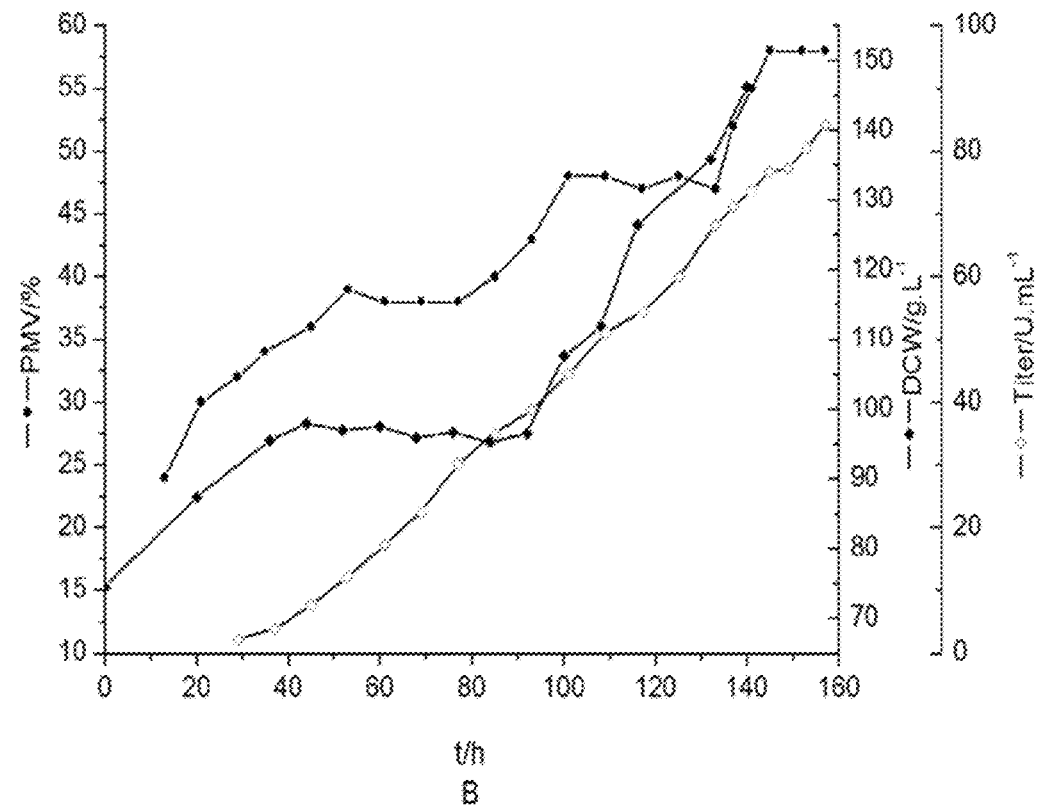

As indicated by FIG. 10a, in the first 10 hours, OUR increased gradually while DO decreased gradually as metabolic activities of the cells became more and more strong. Then, DO was maintained through the increase of gas flow rate and the regulation of agitation speed at about 30%-40% until OUR reached 40.2 mol·L$^{-1}$·h$^{-1}$ at the 52$^{nd}$ hour when the first phase of high oxygen consumption occurred. After then and before the 90$^{th}$ hour, OUR changed little. During the same period, synthesis of cephalosporin C began and the amount of the cells increased continuously. As a result, soybean oil substituted glucose as the main carbon source in the metabolic substrate. As the substrate, fatty acid consumed more oxygen than glucose. Thus, OUR began to increase in a linear pattern from the 92$^{nd}$ hour till approximately the 110$^{th}$ hour when it reached a maximum of 57.1 mol·L$^{-1}$·h$^{-1}$. At this phase, the amount of cephalosporin C obtained through biological synthesis almost increased linearly, consistent with the high activity of the key enzyme for the synthesis of cephalosporin C in this manner. The high oxygen consumption characteristic (OUR at a high level) of the fermentation of cephalosporin C was the most significant at this phase, because oxygen was necessary for several reaction steps during the biological synthesis of cephalosporin C. Therefore, the synthesis of cephalosporin C was strongly influenced by the supply of oxygen (as reflected by dissolved oxygen (DO) in the reactor). A high level of dissolved oxygen indicated that there existed enough oxygen for facilitating the synthesis of cephalosporin C while reducing the content of penicilline N (PEN N), deacetyl oxycephalosporin C (DAOC), deacetyl cephalosporin C (DAC)[2-4], Contrarily, deficient oxygen would lead to significant increase of DAOC, a by-product of fermentation.

2.2 Changes of Metabolic Characteristics of Cells with Varying Carbon Sources During the Fermentation of Cephalosporin C 2.2.1 Analysis of the Correlation between the Shift of Carbon Sources and Parameters During the Fermentation Plots of parameters relevant to varying substrate were obtained during the fermentation of cephalosporin.

Figure 10B:
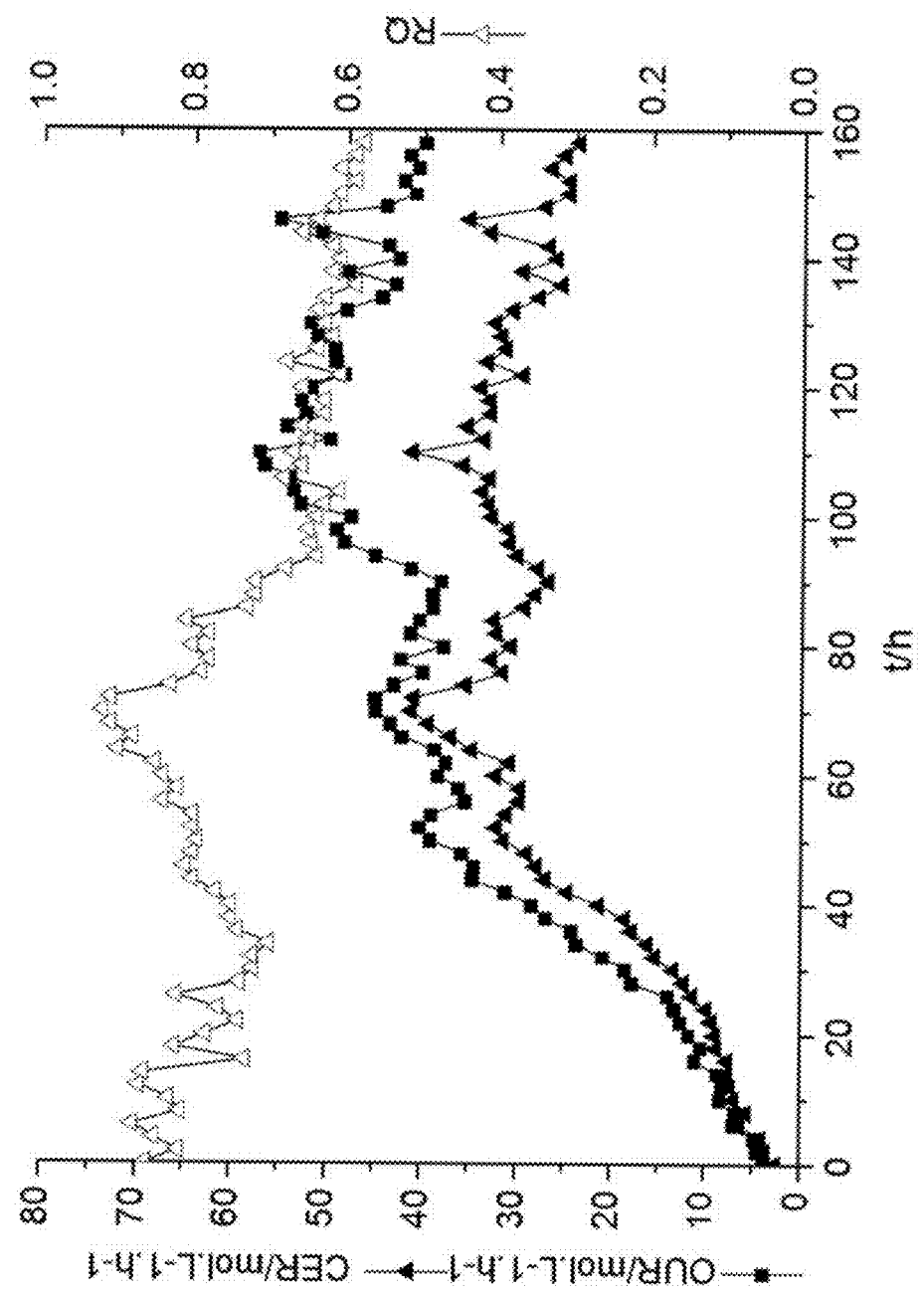

As indicated by FIG. 10b, in the early period of the fermentation, cells grew depending on glucose as the carbon source, which was the product of the hydrolyzation of dextrin. As metabolism of the cells became active gradually, OUR and CER increased correspondingly. Before the 17$^{th}$ hour, RQ was above 0.75, which also indicated the effect of using glucose as the main carbon source[5]. From the 17$^{th}$ hour to the 29$^{th}$ hour, the metabolic rate of the cells accelerated, therefore, glucose resulting from the hydrolyzation of dextrin could not meet the demand of the cells. Thus, the cells had to use free amino acids provided by such nitrogen sources as soybean powder in the culture medium to form their own carbon skeletons, so that RQ decreased. From the 29$^{th}$ hour to the 70$^{th}$ hour, glucose resulting from the hydrolyzation of dextrin as the main carbon source of the cells and several other carbon sources were used, so that RQ increased. Along with the use of dextrin, RQ reached a maximum of 0.95 at about the 70$^{th}$ hour when a shift of substrate began. After 90 hours of fermentation, RQ was almost kept constant at about 0.6, indicating that soybean oil acted as the main substrate of cellular metabolism at this phase.

2.2.2 Function of Supplementing Soybean Oil in the Late Period of the Fermentation and Effect Thereof on Dissolved Oxygen In the production of cephalosporin C by fermenting *Cephalosporium Acremonium*, the supplement and use of soybean oil were important. On the one hand, soybean oil provided the key carbon source for the synthesis of cephalosporin C. On the other hand, as a general defoamer, soybean oil played a significant role in controlling the liquid level of the fermenter in the late period of fermentation. Experimental results showed that soybean oil supplemented at different phases functioned differently. The change tendency of RQ in early fermentation showed that 5% of soybean oil present in the primary culture medium was not used at all in this period (FIG. 10b). Perhaps the function of the existence thereof merely is the induction of lipase.

Soybean oil was supplemented at the $80^{th}$ hour. As fatty acids in soybean oil was used, RQ decreased gradually to 0.64 in late phase of the substrate shift after the $95^{th}$ hour. In the phase when soybean oil acted as the main medium, the fluctuation of RQ was relatively small. This profile was related to the development of the activity of lipase of the cells and the hindrance of high concentration of glucose[6,7]. Specifically, at the beginning of the medium shift (at about the $70^{th}$ hour), the rate of hydrolyzation from soybean oil to fatty acids could not meet the demand of the cells due to the insufficient activity of lipase, leading to a decrease of such metabolic parameters as OUR and CER (FIG. 10b). As the activity of lipase improved, fatty acids as the carbon source that could be used directly increased, leading to a rise of OUR and CER at the $90^{th}$ hour. After OUR and CER reached their maximums at the $110^{th}$ hour, the fermentation process entered a relatively stable phase when the biological synthesis of cephalosporin C was increased greatly.

Correspondingly, when soybean oil was used as the substrate in the fermentation process, oxygen consumed thereby also increased greatly. In order to maintain the DO level, stirrer speed had to be raised several times after the $90^{th}$ hour from 400 rpm to 600 rpm (FIG. 10a), leading to a maximum of OUR in the case of using soybean oil as substrate.

Primary knowledge of the metabolic characteristics and the regulation of the fermentation process of cephalosporin C was gained via the foregoing study. Through regulation of DO and OUR, fermentation unit in the 50 L fermenter was increased to 38000 U/ml.

2.3 Study on the Scale Up of the Fermentation of Cephalosporin C 2.3.1 Difference Between the Metabolic Characteristics of the Fermentation Process of Cephalosporin C in the Laboratory Fermenter and those in the Industrial-Scale Fermenter Based on the full understanding of the metabolic characteristics of cephalosporin C via the study with a 50 L laboratory fermenter, fermentation unit as high as 38000 U/ml was achieved eventually. However, with an industrial-scale fermenter of 160 $m^3$, despite the fact that similar culture measures were taken and the same metabolic characteristics were obtained after some modification of the fermenter, the resulting fermentation unit was 20% lower than that obtained in the 50 L laboratory fermenter (FIG. 10c, in which the unit of each parameter has been converted to be the same).

Figure 10C:
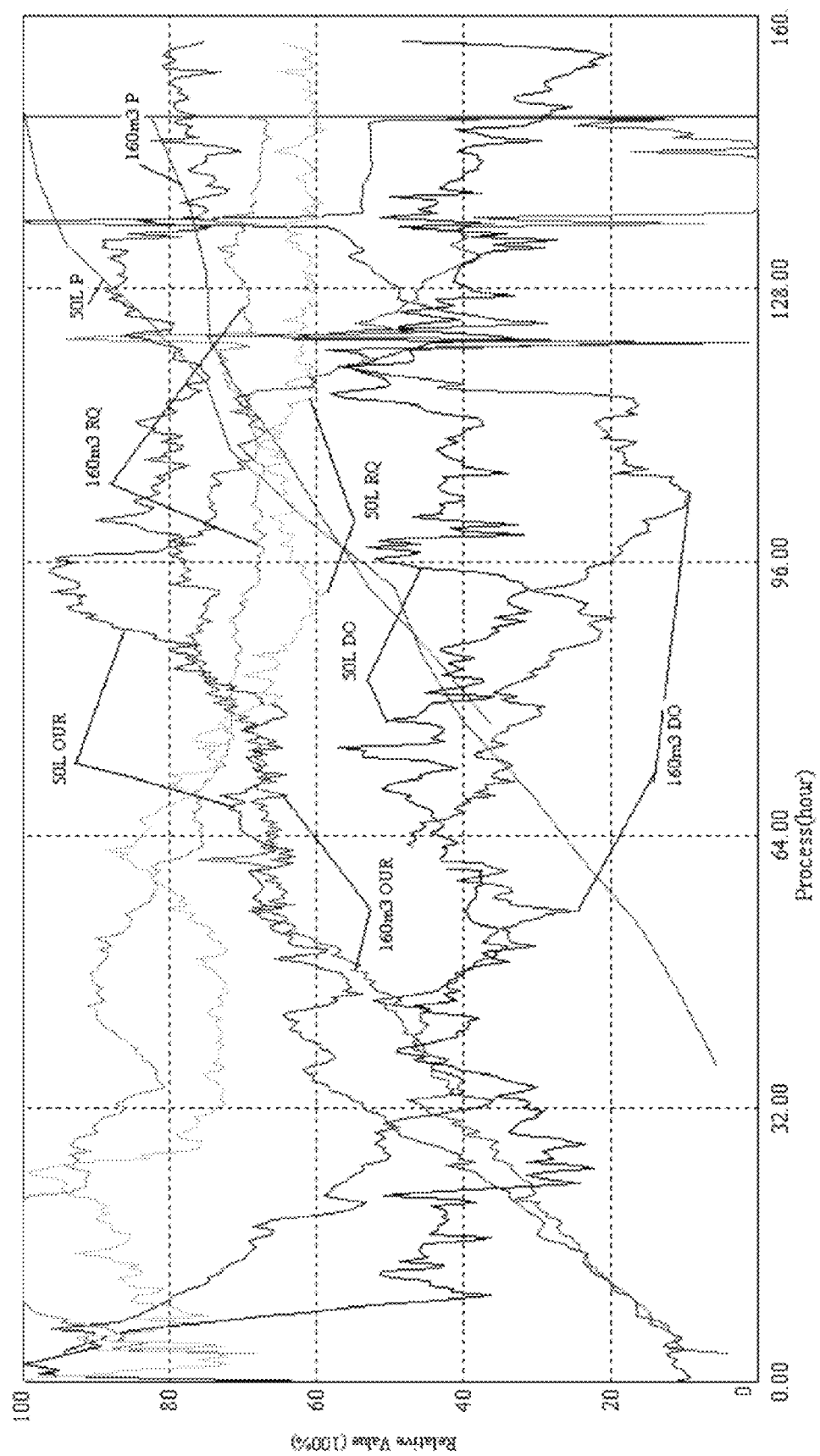
Figure 10D:
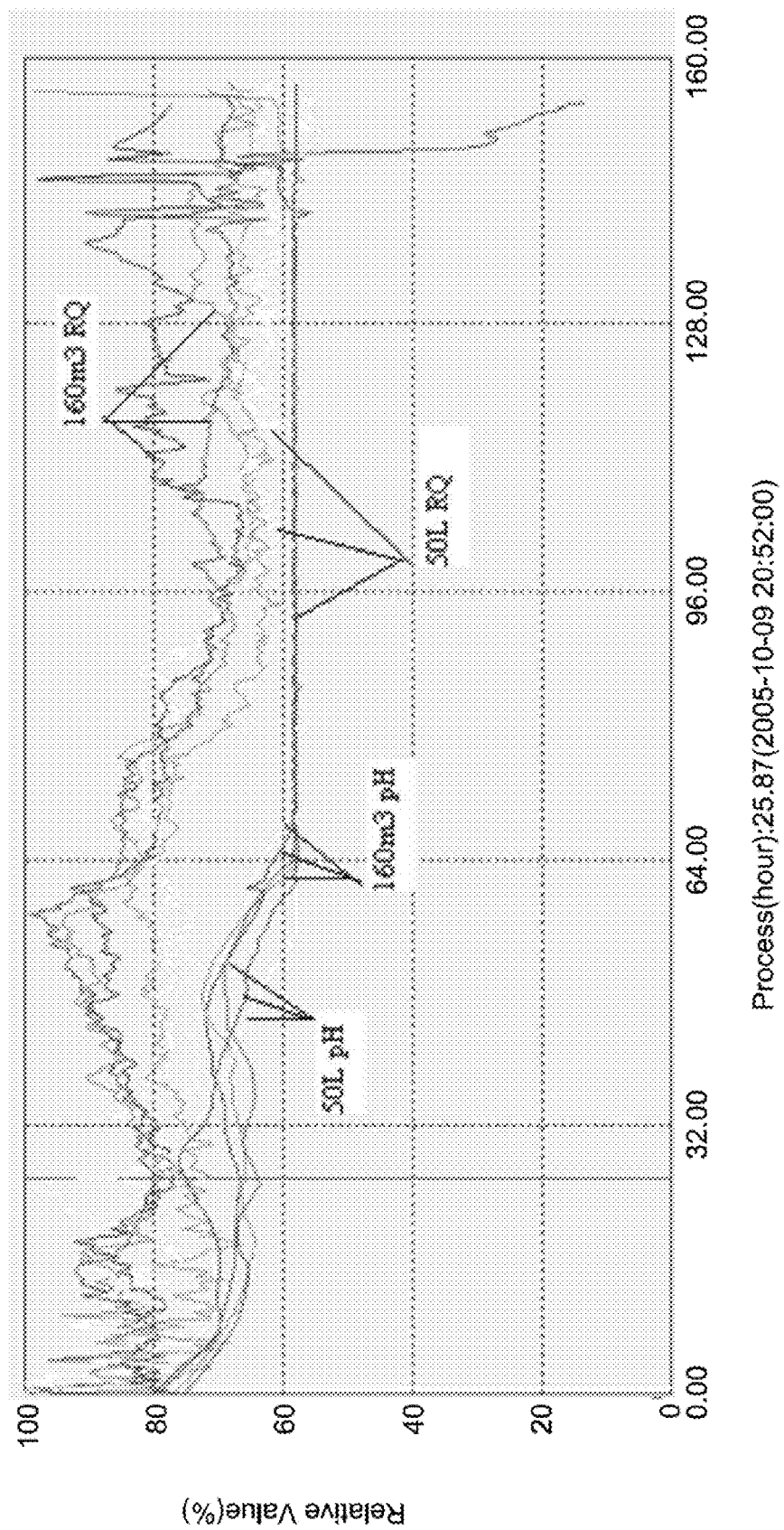
Figure 10E:
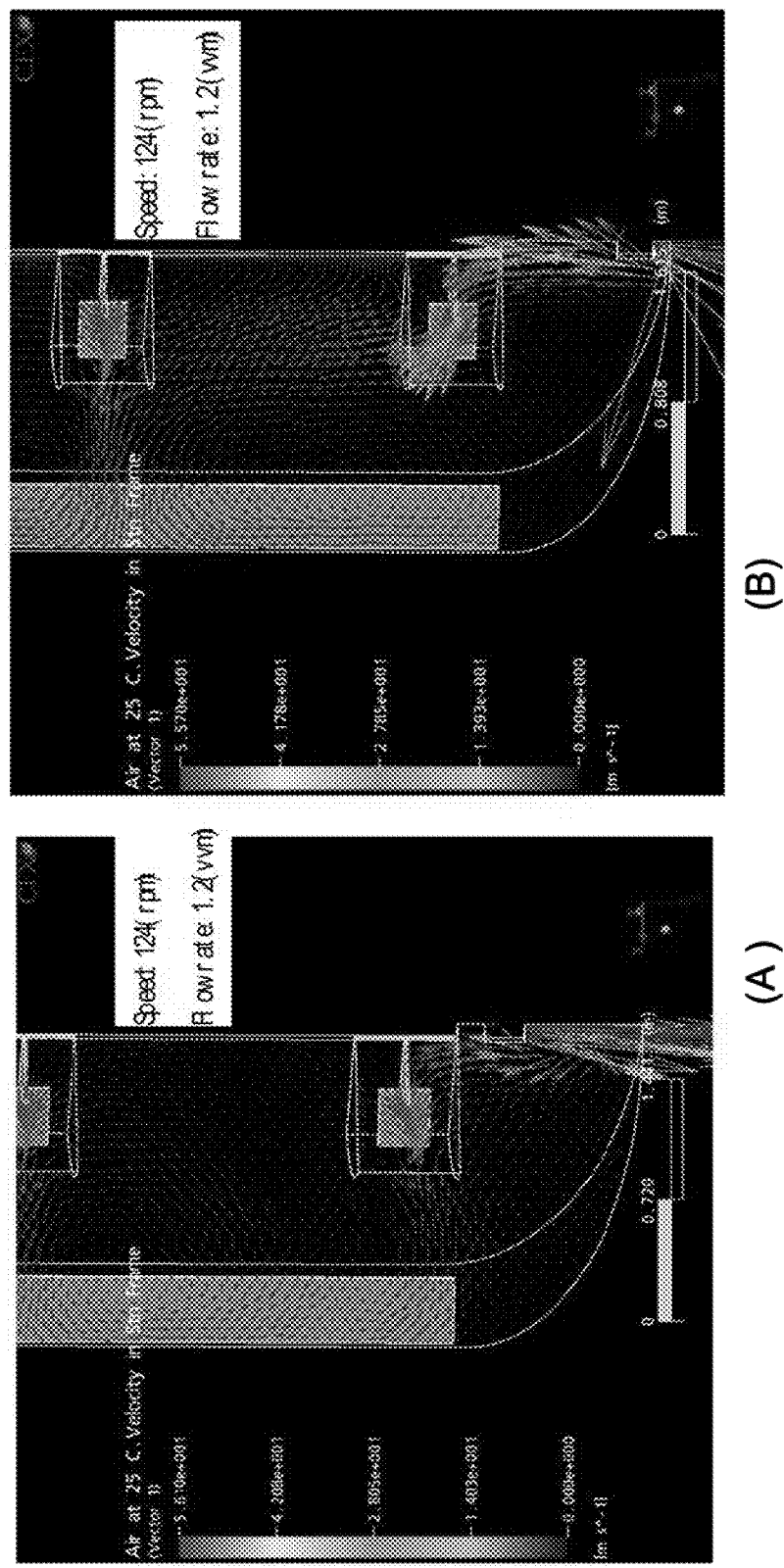

As indicated by FIG. 10c, DO in the 50 L fermenter was maintained stably between 30% and 50% during the whole process. Especially after the $90^{th}$ hour when oil became the main carbon source, OUR was kept relatively high and stably. In contrast, DO in the 160-$m^3$ industrial-scale fermenter decreased to as low as about 10% at the $100^{th}$ hour. In such a case, a general measure that had to be taken was to reduce the supplement of oil. Correspondingly, OUR in the 160 $m^3$ industrial-scale fermenter began to decrease and such a tendency continued in late phase. There were two more curves in FIG. 10c worth noticeable, i.e. the RQ curves of the laboratory fermenter and the large fermenter, respectively. Ever since oil became the substrate in the 50 L fermenter, its RQ was much lower than that of the industrial-scale fermenter, indicating that utility of oil in the laboratory fermenter was relatively better than that in the industrial-scale fermenter. This phenomenon was not rare during the research. FIG. 10d compared the RQ and pH obtained in batches of laboratory studies with the corresponding parameters obtained in batches of industrial-scale fermentation.

As indicated by FIG. 10d, the RQ values obtained in a laboratory fermenter were remarkably lower than those obtained in an industrial-scale fermenter, which meant that utility of oil in the industrial-scale fermenter was poorer than that in the laboratory fermenter. At the same time, the amount of oil (converted into volume ratio) supplemented to the industrial-scale fermenter in the whole process was instead much more than that supplemented to the laboratory fermenter. Since oil was fed from the top of a fermenter gradually, if the agitation in the reactor didn't proceed properly, it was likely that substrate was not distributed evenly in the whole reactor, leading to poor utility of the substrate by *Cephalosporium Acremonium*. In addition, the decrease of pH in the early phase witnessed by the laboratory fermenter tended to be faster than that witnessed by the industrial-scale fermenter, indicating that the cells had stronger metabolic activity in the laboratory fermenter than in the industrial-scale fermenter. The shape of an agitating paddle was reported to have a considerable influence on oxygen supply and mixing in the fermentation process. Thus, the variation tendency of the foregoing parameters aroused our doubt on the industrial-scale fermenter about its capability of oxygen-supplying and mixing. Despite the power input was as high as 3 kW/$m^3$, the agitator of the industrial-scale fermenter might have not met the demand of cephalosporin C on high consumption of oxygen.

Figure 10F:
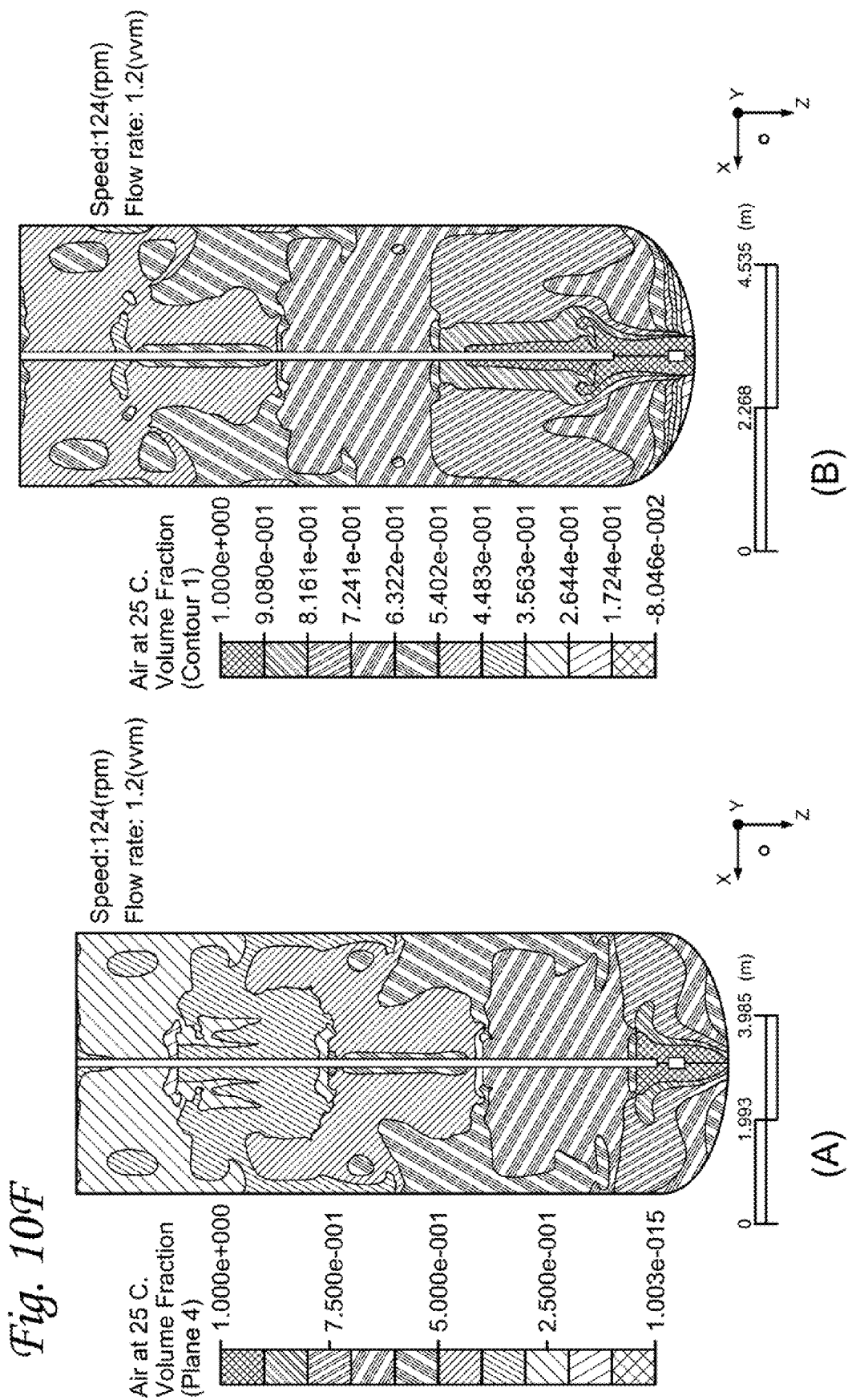

2.3.2 Modification of the Industrial-Scale Fermenter Based on the Analysis of the Metabolic Characteristics of the Cells According to the results of the foregoing simulation, the invention provided a method for adjusting DO and OUR. Specifically, the method included modifying the shapes of the agitating paddles, each originally having four horizontal vanes (radial), wherein the lower two tiers of paddles combined semicircular shape and flat shape for the main purpose of breaking bubbles, and were enlarged in diameter appropriately, and the upper two tiers of paddles each consisted of four vanes for the main purpose of agitating axially. The flow field of the modified reactor with newly designed paddles was simulated and the results were shown in FIG. 10f. As indicated by the figure, owing to the modification of paddle shape, air distribution was improved greatly, the content in the whole fermenter was relatively uniform, and mixing of the fluid in the fermenter was improved.

Figure 10G:
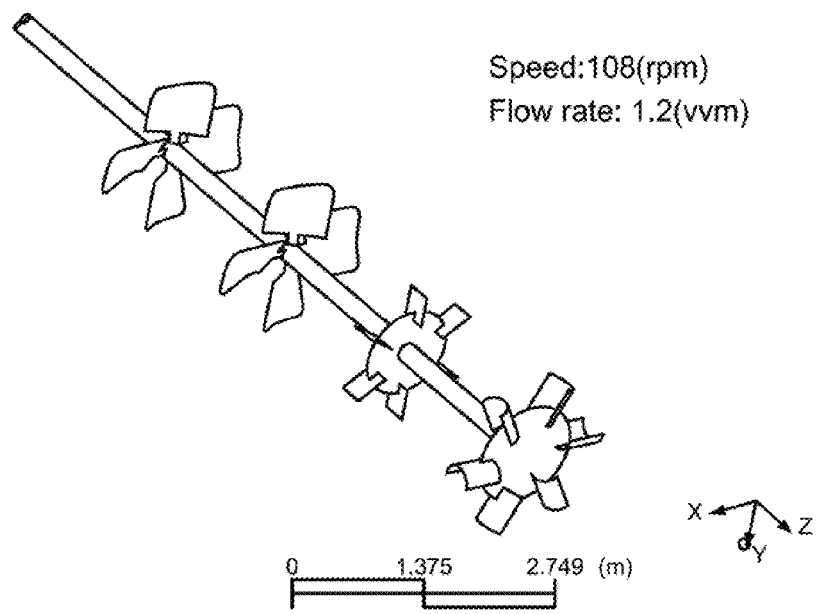
Figure 10G:
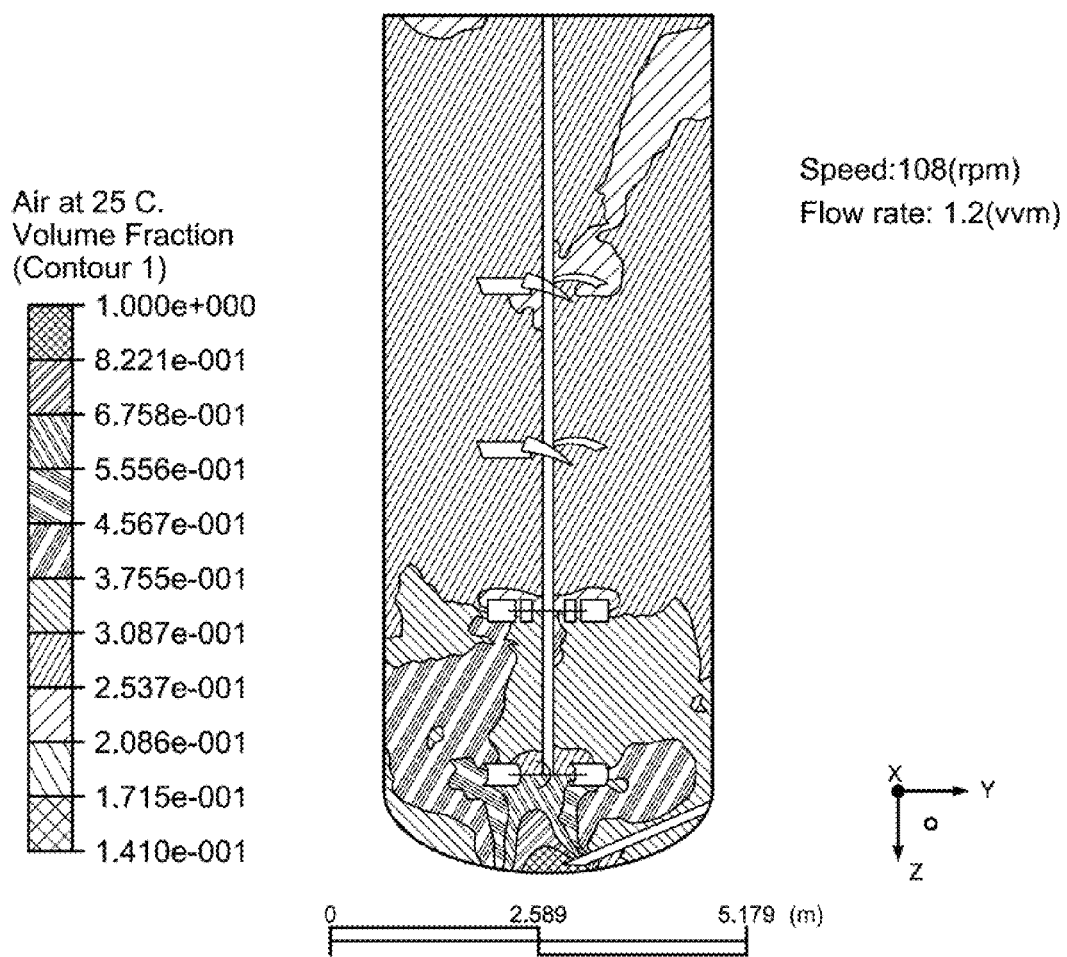

However, as a matter of fact, modification of paddle shape of an industrial-scale fermenter was limited by its original structure design. In other words, paddle shape could not be changed. In such a case, the only choice was to change paddle diameter, i.e. enlarge paddle diameter, so as to improve oxygen supply and mixing. Primary results of the modification were shown in FIG. 10g.

Figure 10H:
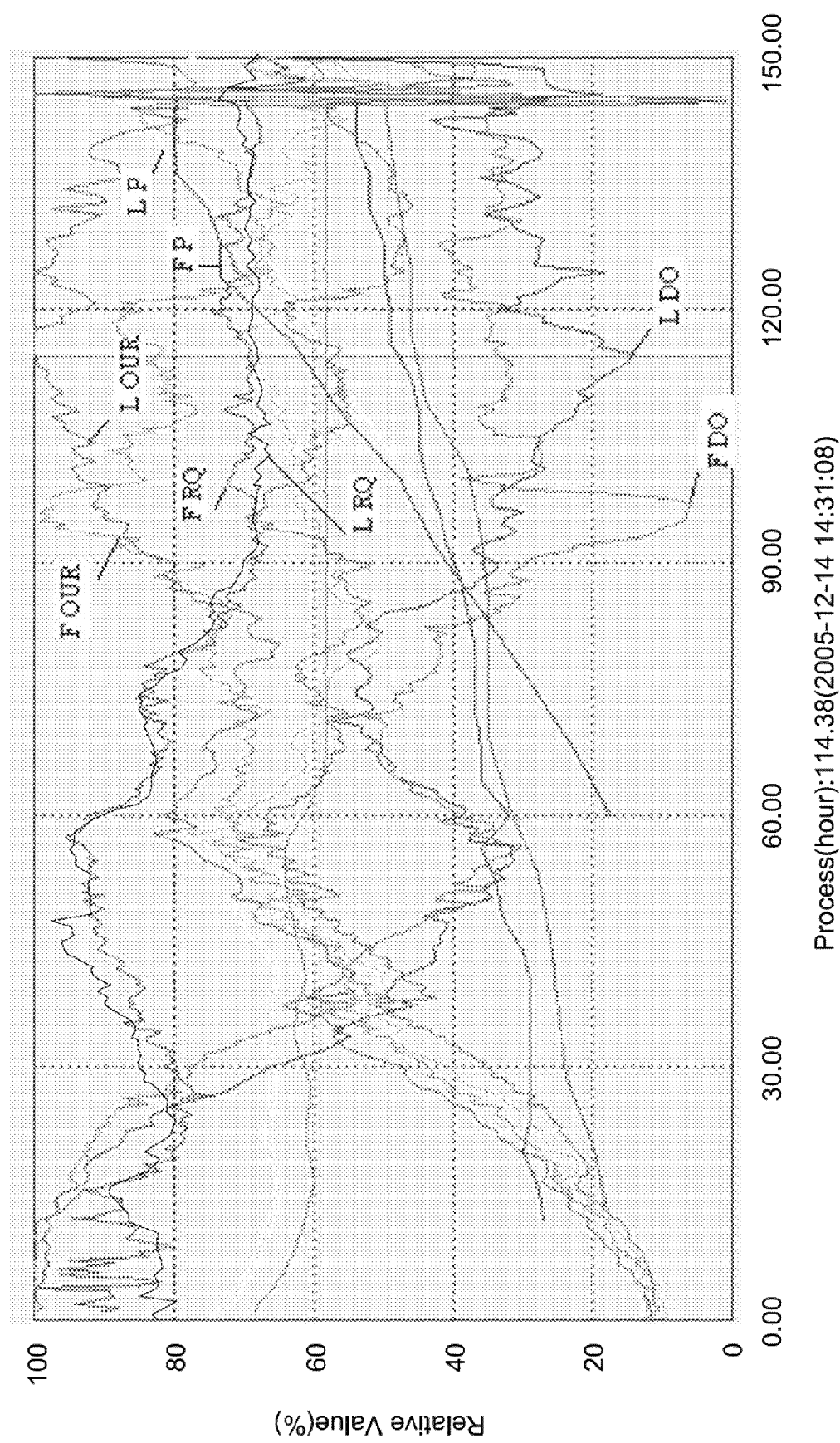

As indicated by FIG. 10h, after the improvement of the agitation, the low end of DO was improved, and OUR was maintained to certain extent, so that DO and OUR in the industrial-scale fermenter were less different with predetermined values (DO and OUR obtained in a laboratory fermenter), and the final fermentation unit increased by 14%. This meant a success of the primary scale-up.

3. Discussion

The invention studied the high oxygen consumption characteristic in the production of cephalosporin C from *Cephalosporium Acremonium* and its influence on various parameters, the influence of supplementing oil in the fermentation process on the production, the shift of carbon source substrate in the fermentation of cephalosporin C and the characteristics of the resulting relevant parameter changes. After measures were finally taken to bring the physiological characteristics of the industrial-scale fermenter close to those of the laboratory fermenter, scale-up of the fermentation process was achieved.

(1) Since the fermentation of cephalosporin is a process with high oxygen consumption, dissolved oxygen not only had an influence on the metabolic activities of the growth of the cells, but also on the yield of cephalosporin C. As the same time, low concentration of dissolved oxygen would lead to increase of by-products such as PEN N, DAOC and DAC, which would not only go against the quality of the product, but also bring trouble to subsequent separation and purification. Thus, sufficient supply of oxygen was particularly important during biosynthesis, particularly in middle and late phase of the fermentation when soybean oil was used as the main carbon source, which incurred high consumption of oxygen.

(2) Since soybean oil was the key carbon source desired in the biosynthesis of cephalosporin C, utility of soybean oil in various periods could be understood via analysis of the function of soybean oil in various phases and its influence on various parameters. Specifically, soybean oil added in the initial feed could induce the production of lipase, which facilitated the utility of soybean oil. In early phase, the products of the hydrolyzation of dextrin such as glucose were the main carbon source. In middle phase of the fermentation, the cells underwent active metabolism, so that the need for substrate increased, and a great deal of soybean oil was consumed as the basic carbon source. At the same time, when soybean oil acted as the main substrate, the need for dissolved oxygen was great in cellular metabolism. Thus, a higher requirement of oxygen supplying ability was put on the equipment. On the other hand, with respect to a fermenter having a weight of 160 tons and a height of over 10 meters, when soybean oil was added from the top of the fermenter, a higher requirement of mixing ability was put on the fermenter to distribute the substrate in the reactor uniformly.

(3) In the scale-up, it was found first that the industrial-scale fermenter had a weaker ability of supplying oxygen than the laboratory fermenter via comparing the metabolic characteristics of the laboratory fermenter and the industrial-scale fermenter. Then, by changing paddle diameter, oxygen supply and mixing were both improved, and DO and OUR in the industrial-scale fermenter were close to those in the laboratory fermenter. Thus, scale-up of the fermenter was affected primarily.

Example 4

Optimization and Scale-Up of the Fermentation Process of $VB_{12}$

1 Materials and Methods 1.1 Strain and Culture Media
1.1.1 Strain:
*Pseudomonas denitrificans*, available from Huarong Pharmaceuticals Co. affiliated to Shijiazhuang Pharmaceuticals Group.
1.1.2 Culture Media
Primary seed culture medium: molasses, corn steep liquor, $KH_2PO_4$, $(NH_4)_2SO_4$, $(NH_4)_2HPO_4$, $MnSO_4$, etc.
Secondary seed culture medium: molasses, corn steep liquor, $KH_2PO_4$, $(NH_4)_2SO_4$, $(NH_4)_2HPO_4$, $MnSO_4$, etc.
Fermentation culture medium: molasses, sucrose, betain, $(NH_4)_2SO_4$, $MgSO_4$, $CoCl_2$, DMBI, $ZnSO_4$, etc.

1.2 Fermenter:
A 9 $m^3$ pilot fermenter with an axially positioned agitator; a 120 $m^3$ industrial-scale fermenter with an agitator for mixing axially for most part (FIG. 4).
1.3 Analysis Methods
1.3.1 Measurement of Biomass:
Measurement of cell dry weight (DCW), wherein 25 mL fermentation broth was sampled and centrifuged, the cells were washed with distilled water, and after centrifuged once again, the cells were dried at 105° C. to a constant weight which was then weighed.
1.3.2 Measurement of Total Sugar:
Fehling test.
1.3.3 Measurement of $NH_2$—N:
Titration with formaldehyde.
1.3.4 Exhaust Gas Analysis:
SIMENS GXH-9022 system was used for analyzing $CO_2$, $O_2$, with final data being processed and analyzed using an upper computer software package BIOSTAR (available from National Biochemical Engineering Technologies Research Center of East China University of Science and Technology).
1.3.5 Measurement of Dissolved Oxygen:
Mettler Toledo in-situ dissolved-oxygen detecting system.
1.3.6 Measurement of pH:
Mettler Toledo in-situ pH detecting system.
1.3.7 Measurement of $VB_{12}$
Various forms of $VB_{12}$ in a sample to be measured were converted into cyanocobalamin. Mobile phase: 250 mM phosphoric acid solution:acetonitrile=30:70; chromatographic column: C8 5FI13513 260×4.6 mm; detection wavelength: 361 nm; sample volume: 20 μl; flowing rate: 1.7 ml/min.

2. Results and Analysis 2.1 Effect of Oxygen Supply in Shake Flask on the Production of $VB_{12}$ Via Fermentation Since the synthesis of $VB_{12}$ from *P. denitrificans* is a metabolic process involving oxygen consumption, addition of oxygen atoms is required in the aerobic synthesis of $VB_{12}$. However, the effect of oxygen supply on the synthesis of $VB_{12}$ by fermenting *P. denitrificans* has not yet been reported. Thus, in this experiment, the amount of fermentation broth and the inoculum amount were kept consistently in shake-flasks during the fermentation process, and agitator speed was varied at different fermentation phases in order to study the effect of oxygen supply on the synthesis of $VB_{12}$. Specific experimental design and results were given in Table 3:

TABLE 3

Effect of Different Revolutions per Minute in Shake-flask Fermentation on $VB_{12}$ Biosynthesis

| Revolution speed at different fermentation phases /(rpm) | | | $VB_{12}$ | Relative |
|---|---|---|---|---|
| 0-60 h | 60-100 h | 100-160 h | (μg/ml) | percentage |
| 260 | 260 | 260 | 125.45 | 100% |
| 200 | 200 | 200 | 95.45 | 76.08% |
| 260 | 260 | 200 | 121.57 | 96.90% |
| 200 | 200 | 260 | 96.82 | 77.18% |
| 200 | 260 | 260 | 116.46 | 92.84% |
| 260 | 200 | 200 | 108.60 | 86.57% |

As indicated by Table 3, when the revolution speed was kept at 200 rpm during the shake-flask fermentation process, the final concentration of $VB_{12}$ was the lowest. When the revolution speed was kept at 260 rpm during the shake-flask fermentation process, the final concentration of $VB_{12}$ was the highest among the six cases, 24% higher than the control. Substantive synthesis of $VB_{12}$ by *P. denitrificans* occurred from the $60^{th}$ hour to the $100^{th}$ hour in the shake-flask fermentation process. As indicated by Table 3, oxygen supply in this fermentation phase had critical effect on the final concentration of $VB_{12}$. In three cases where the revolution speed was set at 200 rpm in this phase, the final concentrations of $VB_{12}$ were relatively low, compared with the other three cases where the revolution speed was set at 260 rpm in this phase. From the above experimental results, it can be drawn that better supply of oxygen in the shake-flask fermentation process does more favor to the biosynthesis of $VB_{12}$.

Figure 11A:
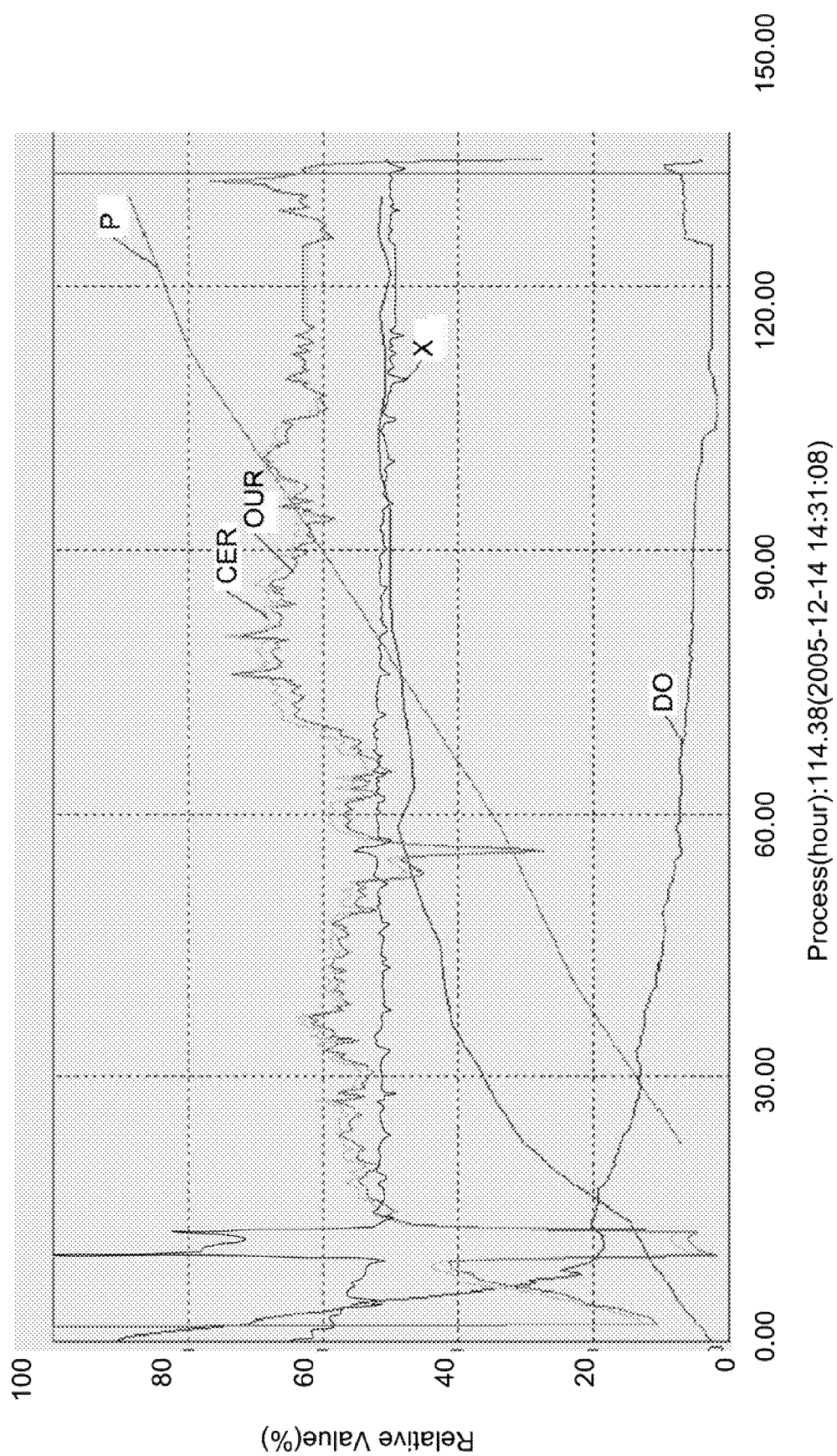

2.2 Effect of Oxygen Supply and Consumption on Metabolism of *P. Denitrificans* in a 9 $m^3$ Pilot Fermenter Based on the knowledge from the shake-flask study that oxygen supply is important for the metabolism of *P. denitrificans* during its fermentation process, a corresponding experiment was done on a 9 $m^3$ pilot-scale fermenter installed with a software package BIOSTAR for analyzing data from the fermentation process, and a representative metabolic curve was obtained as shown in FIG. 11a.

As can be seen from the curve, during the fermentation of *P. denitrificans*, along with the continuing increase of cell amount (X), oxygen uptake rate (OUR) and carbon dioxide evolution rate (CER) increased continuously, while DO decreased continuously. At about the $20^{th}$ hour, DO decreased to a relatively low level (about 20%). Then, OUR and CER reached a relatively high level. As the fermentation continued, at about the $80^{th}$ hour, OUR and CER increased a little again, and DO also decreased further (about 8%). In the final phase of the fermentation, the actual increase of cell amount was not noticeable (the increase of X was rather mild), but OUR and CER continued to stay at a relatively high level. At the same time, $VB_{12}$ continued to increase at a relatively high rate, indicating that the synthesis of $VB_{12}$ is indeed a process consuming a great deal of oxygen. Under such conditions, the final concentration of $VB_{12}$ reached 195 μg/ml.

2.3 Study on Scale-Up to Industrial Scale Based on the Same Oxygen Consuming Characteristics An experiment for scale-up was done on a 120-$m^3$ industrial-scale fermenter, and the following results were obtained for metabolism under different conditions.

Figure 11B:
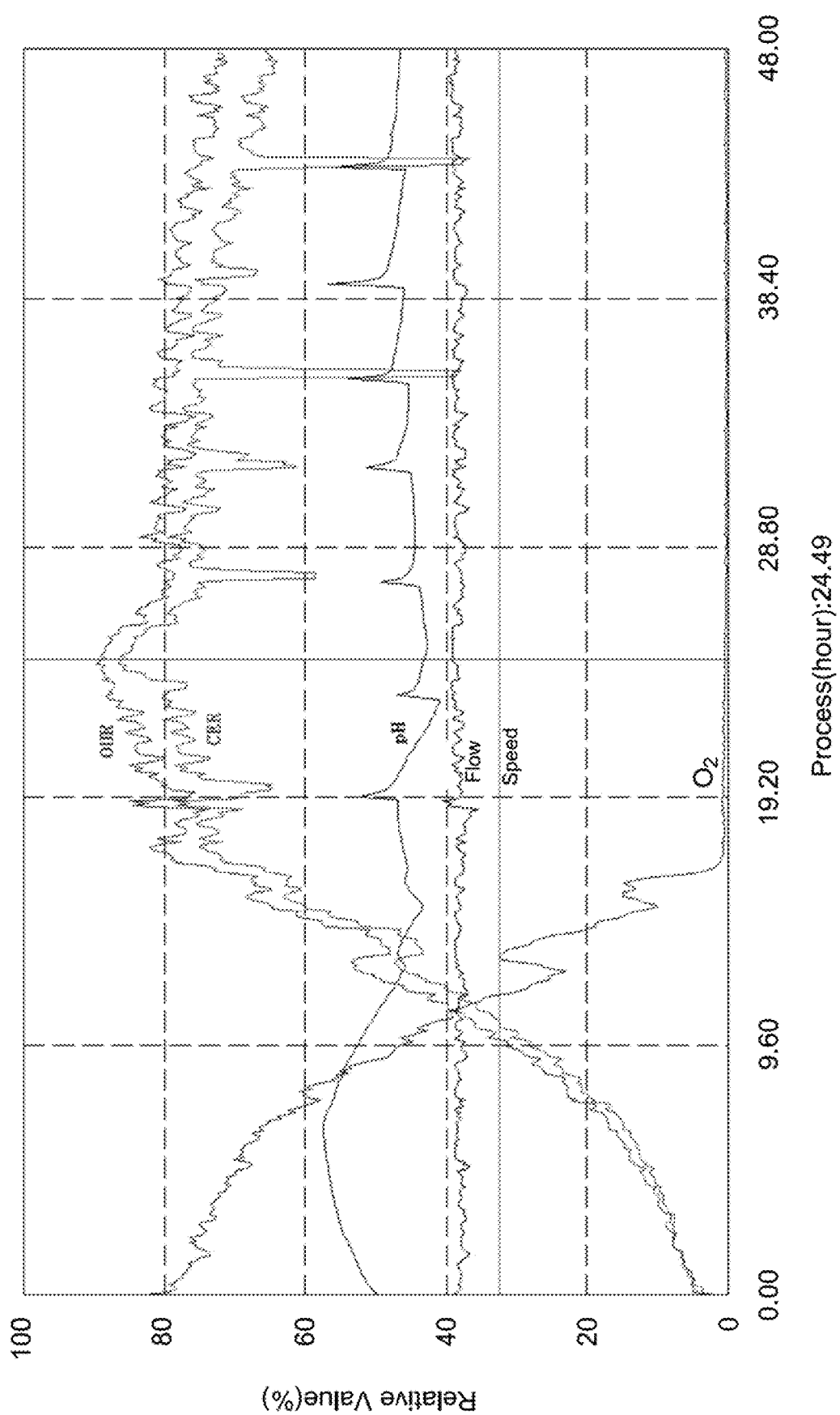
Figure 11C:
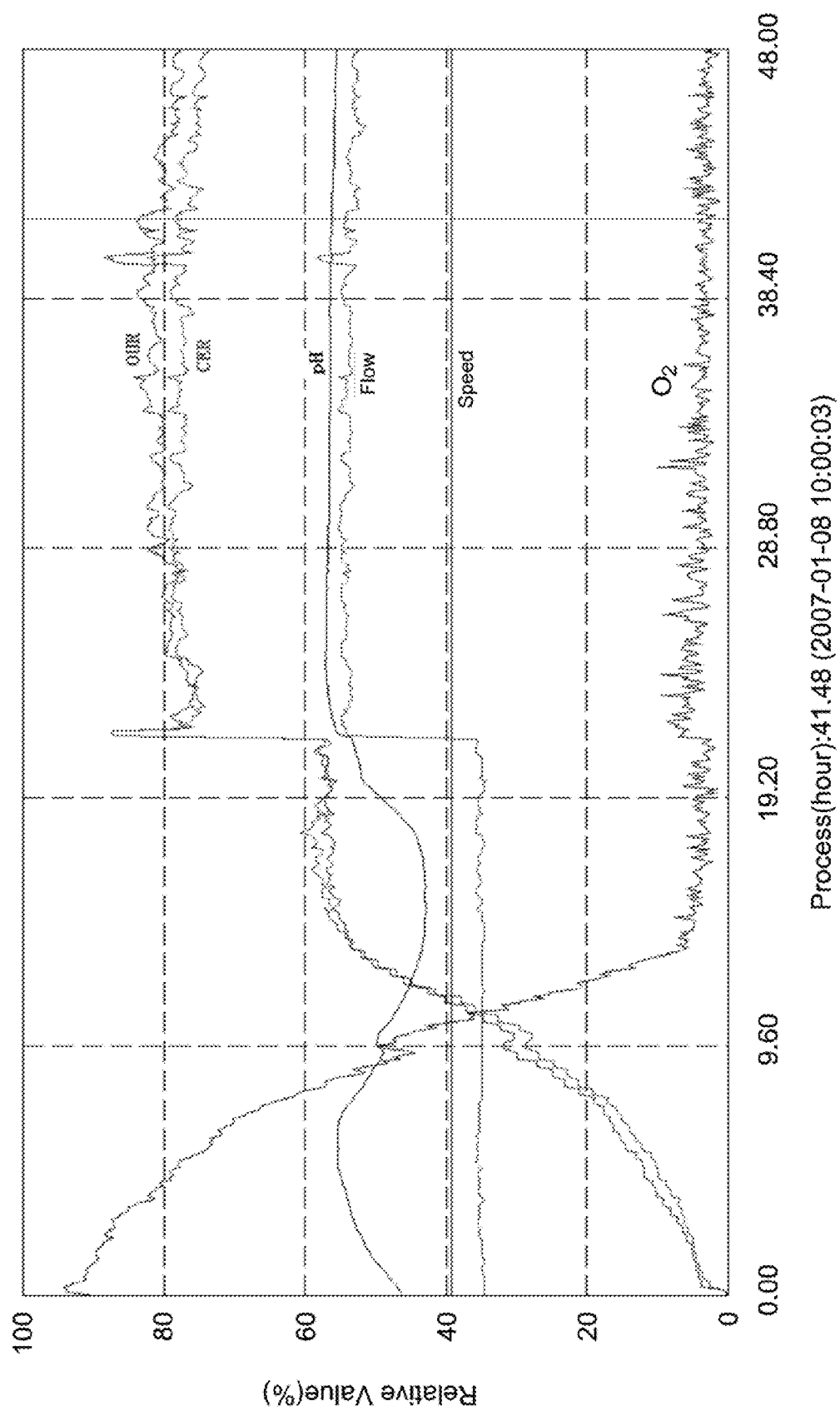

2.3.1 Changes of OUR, CER, DO and pH in Early Phase of Fermentation at Two Different Oxygen-Supply Levels FIGS. 11b and 11c showed the change of OUR, CER, DO and pH obtained by in-situ measurements in early phase of the fermentation in the 120 $m^3$ fermenter at two different oxygen-supply levels.

As indicated by FIGS. 11b and 11c, the lag phase of *P. denitrificans* was very short. After the cells began to grow, pH continued to increase until a peak was reached. Then pH began to decrease gradually, after which pH began to increase again and then began to decrease again. At low oxygen-supply level as shown in FIG. 11b, due to the continuous decrease of pH, a suitable pH of the fermentation broth had to be maintained by adding aqueous ammonia, so that pH varied in a zigzag pattern. In contrast, in the case of better supply of oxygen (FIG. 11c), pH was quite stable after 20 hours, and there was no need to adjust pH by adding aqueous ammonia as in the case where oxygen-supply level was low. A possible explanation for this is that less organic acids were accumulated due to complete metabolism of sugar under better supply of oxygen, so that pH was kept stably. With respect to the change of DO, as DO decreased during the growth of the cells, CER and OUR increased gradually at the same time. As shown in FIG. 11b, when DO decreased to 0 at the $17^{th}$ hour, OUR and CER still tended to increase until they reached their peaks of 46 mol/(hm$^3$) and 44 mol/(hm$^3$) respectively at the $24.5^{th}$ hour. After the $24.5^{th}$ hour, OUR and CER began to drop remarkably, possibly due to the fact that the metabolic activities of the cells were restricted by oxygen supply. The final concentration of $VB_{12}$ in this batch was 125 μg/ml. As shown in FIG. 11c, the change of DO was identical to that in FIG. 11b, but DO in this case experienced a greater drop at the $15^{th}$ hour (about 5%). OUR and CER were promoted to a new high level by increasing gas flow rate during the process, and OUR and CER exhibited no obvious tendency to drop. This meant that active metabolism of the cells had been maintained, which was more desirable for the biosynthesis of $VB_{12}$. The final concentration of $VB_{12}$ in this batch was 190 μg/ml.

2.3.2 Evaluation of Scale-Up—Changes of Total Sugar, $NH_2$—N, Cell Dry Weight, $VB_{12}$ and the Like in Fermentation at Two Different Oxygen-Supply Levels Corresponding to the foregoing test results, the changes of total sugar, $NH_2$—N, cell dry weight and $VB_{12}$ were measured in two cases where dissolved oxygen was controlled at different levels. The results were given in FIG. 11d.

Figure 11D:
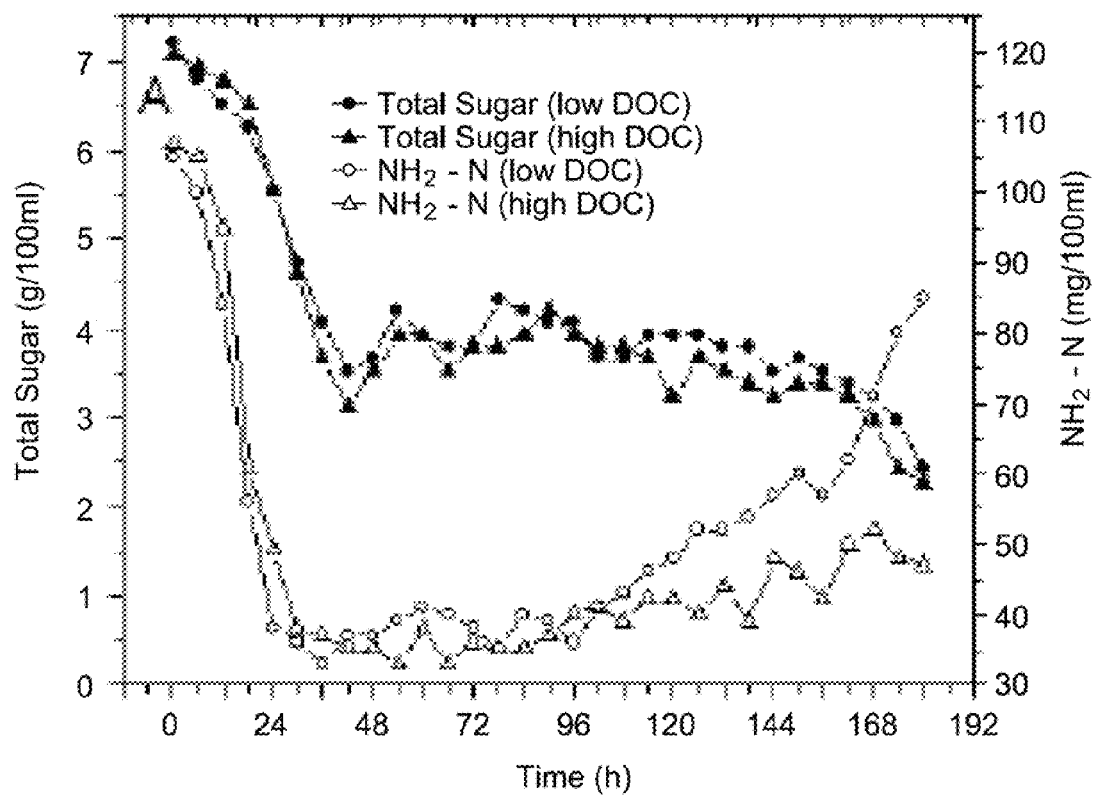
Figure 11D:
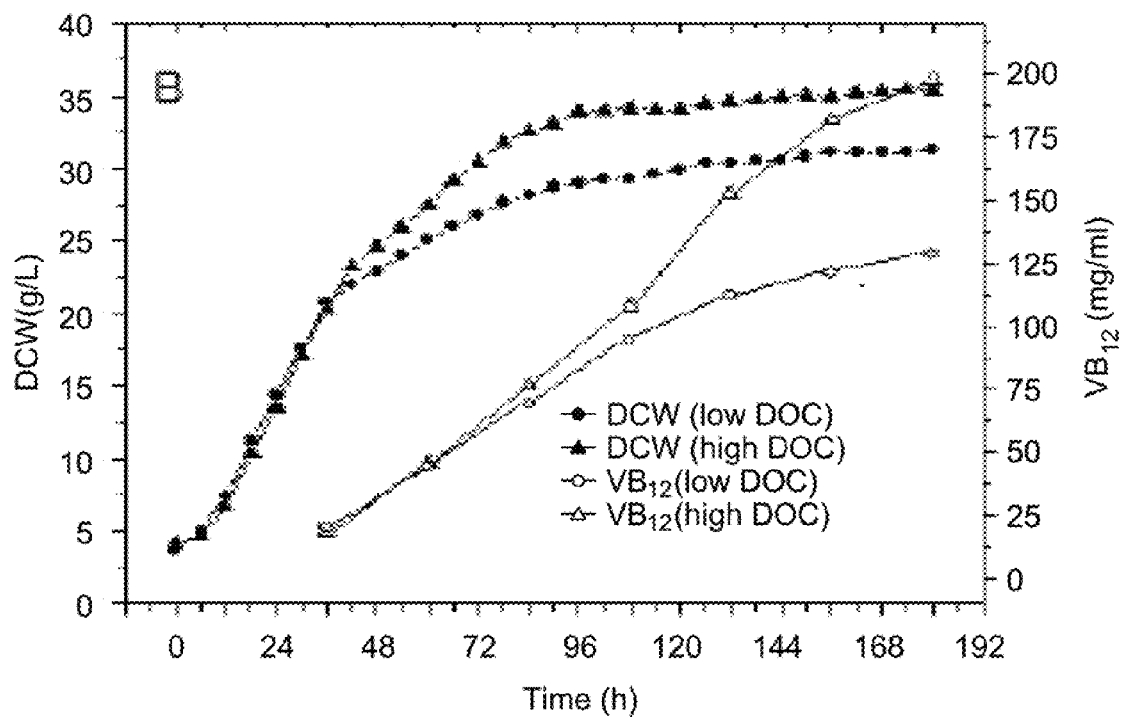

The total sugar concentration in the fermentation broth was kept at 3-4 g/100 ml in the fermentation process by supplementing sugar when the total sugar concentration dropped to about 4 g/100 ml. As indicated by FIG. 11d (A), sugar consumption was similar in early phase of the fermentation for the two cases, although it was slightly better in the case where oxygen supply was low, probably due to the better nature of the strain in this case. However, after 20 hours, sugar consumption rate was better in the case where oxygen supply was high than in the case where oxygen supply was low. With respect to the change of $NH_2$—N in the fermentation process, $NH_2$—N content was lower in the case where oxygen supply was low than in the case where oxygen supply was high in the first 36 hours, but the situation was reversed after that, especially after 120 hours when $NH_2$—N content in the fermenter where dissolved oxygen was controlled at a low level rose back abruptly. The change of $NH_2$—N content also demonstrated the difference of the cell metabolism in these two fermenters. After the $36^{th}$ hour, the metabolic ability of the cells in the fermenter where dissolved oxygen was controlled at a low level dropped significantly due to the restriction of dissolved oxygen. Furthermore, this restriction aggravated the autolysis of the cells after the $120^{th}$ hour.

As indicated by FIG. 11d(B), before the $30^{th}$ hour, cell dry weight was slightly higher in the case where oxygen supply was low than in the case where oxygen supply was high. This result correlated well with sugar consumption, $NH_2$—N content and the like in this period. However, since the $30^{th}$ hour, cell dry weight had been higher in the case where oxygen supply was high than in the case where oxygen supply was low. The highest cell dry weights in these two cases were 35.44 g/L and 31.26 g/L respectively. This demonstrated again that, owing to such factors as seed quality, etc., the metabolic activity of the cells in the fermenter where oxygen supply was low was superior to that in the fermenter where oxygen supply was high in early phase of the fermentation. However, increasing cells required more and more oxygen to satisfy the metabolic demand of the growing cells. The fermenter where oxygen supply was low, if no process adjustment was made, did not have the capability of supplying sufficient oxygen to meet such a demand. As a result, dissolved oxygen was totally depleted. In such a case, dissolved oxygen became a factor that restricted the metabolism of the cells. Now referring to the biosynthesis of $VB_{12}$, the concentration of $VB_{12}$ was slightly higher in the fermenter where oxygen supply was low than in the fermenter where oxygen supply was high, i.e. 20.13 µg/ml versus 18.65 µg/ml, at $36^{th}$ hour. However, after the $60^{th}$ hour, the situation was reversed, especially after the $108^{th}$ hour when the concentration of $VB_{12}$ in the fermenter where oxygen supply was high increased at a significantly higher rate. The final concentration of $VB_{12}$ in the fermenter where oxygen supply was high was 190 µg/ml, 50% higher than that in the fermenter where oxygen supply was low.

From the changes of total sugar, $NH_2$—N, cell dry weight, $VB_{12}$ and the like in the two cases at different oxygen supply levels, an apparent conclusion can be drawn that, in early phase of *P. denitrificans* fermentation when the cells exhibit the most significant aerobicity?, the metabolism of the cells would be restricted drastically if the demand of the cells on oxygen could not be met. Even worse, the cells would autolyze too early, and the synthesis of $VB_{12}$ would also be affected. Accordingly, we adjusted a gitating speed and air flow rate in the fermentation process to improve oxygen supply, mixing and mass transfer. The cell growth and the synthesis of $VB_{12}$ in the fermentation process was enhanced by ensuring oxygen supply and consumption, especially improving oxygen supply.

Figure 11E:
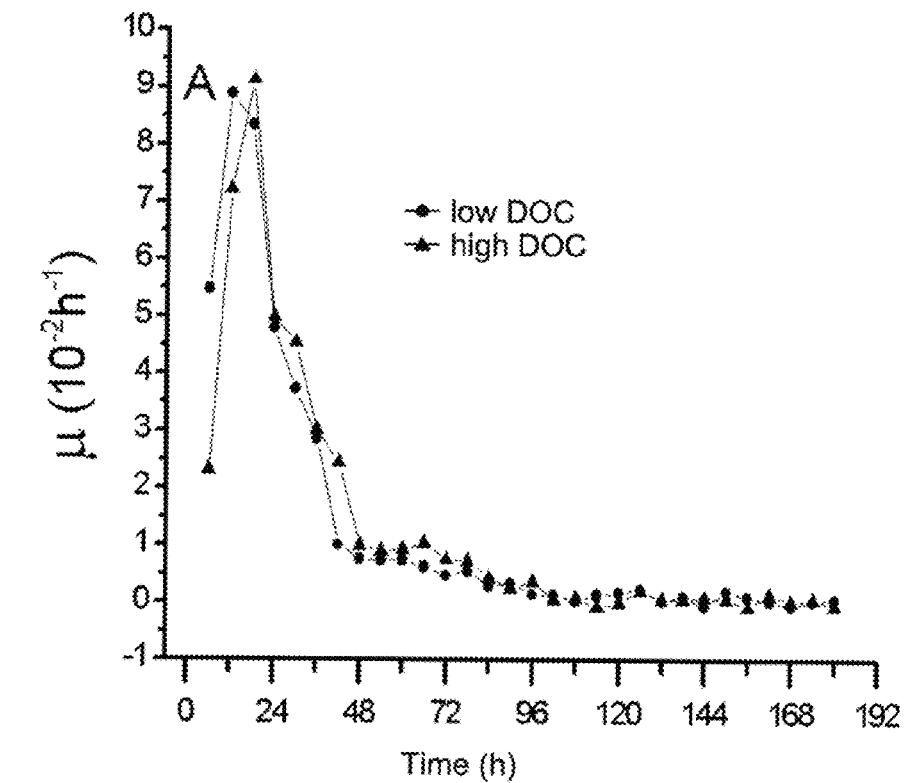
Figure 11E:
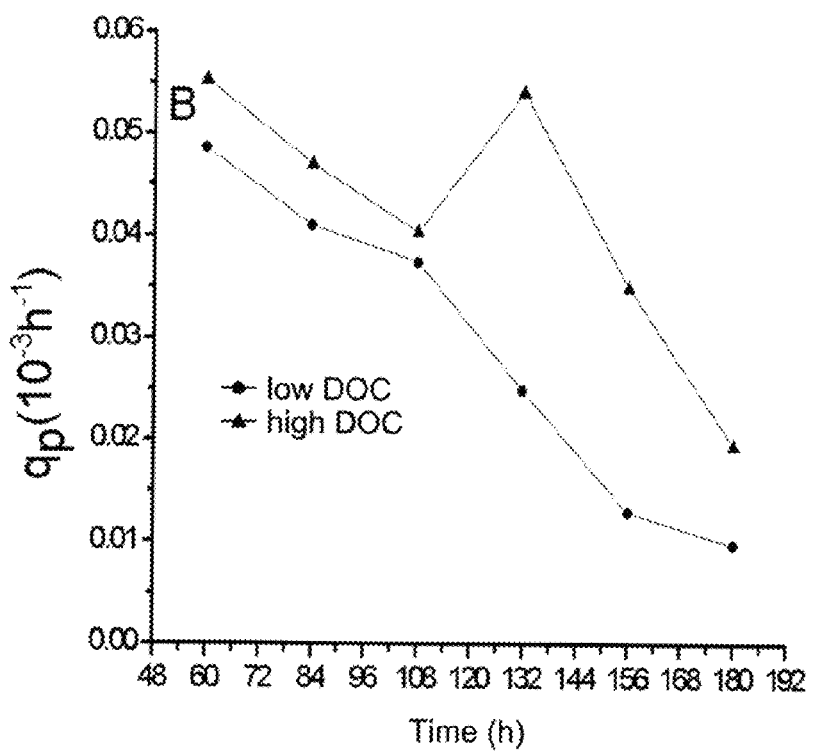

2.3.3 Changes of Specific Growth Rate and Specific Product Forming Rate in Fermentation at Two Different Oxygen-Supply Levels In the foregoing two cases with different oxygen supply levels, µ and $q_p$ in the fermentation process were given in FIG. 11*e*.

As indicated by FIG. 11*e*(A), the specific growth rate in the case where oxygen supply was low reached a maximum of $8.89 \times 10^{-2}$ h$^{-1}$ just at the $12^{th}$ hour, while that in the case where oxygen supply was high reached a maximum of $9.13 \times 10^{-2}$ h$^{-1}$ at the $16^{th}$ hour. In the phase when the cells grew actively, the specific growth rate was always higher in the case where oxygen supply was high than in the case where oxygen supply was low. The specific growth rates of the cells in these two cases were lower than $1 \times 10^{-2}$ h$^{-1}$ after the $48^{th}$ hour, and even close to 0 after the $96^{th}$ hour. As indicated by FIG. 11*e*(B), in the whole fermentation process, $q_p$ was always higher in the case where oxygen supply was high than in the case where oxygen supply was low. The results demonstrated again that, in the production of $VB_{12}$ by fermenting *P. denitrificans*, the cell growth and the synthesis of $VB_{12}$ were seriously affected by oxygen supply, and they could be enhanced by improving oxygen supply level in the fermentation process.

2.3.4 Scaling Up by Adjusting Characteristic Parameters

Similar to Example 3, the parameters concerning the metabolic characteristics in the 120 m$^3$ industrial-scale fermenter were adjusted to ensure the coincidence of oxygen supply having predetermined value with OUR. The concentration of $VB_{12}$ was increased by 50% from 125 µg/ml before the process modification to 190 µg/ml after that.

3. Conclusions

Although there are many reports on the synthesis of $VB_{12}$ from *P. denitrificans*, most of them concentrate on the approaches for synthesizing $VB_{12}$ and improving the level of $VB_{12}$ via random mutagenesis and genetically engineering means. Among the few reports on the real-time regulation of the metabolic process on the whole in the production of $VB_{12}$ from *P. denitrificans*, most were limited within optimization of culture media and the like. The invention focused on the effects of oxygen consumption characteristic of the cells in the macro metabolic regulation of the fermentation on the production of $VB_{12}$ by fermenting *P. denitrificans*.

The effect of oxygen supply on the synthesis of $VB_{12}$ was explored by testing *P. denitrifican* in a shake flask, and the results demonstrated that better supply of oxygen favored the synthesis of $VB_{12}$. Then, by correlation analysis of parameter changes of the fermentation in a 9 m$^3$ medium-scale fermenter, it was discovered that oxygen supply and the tendency of OUR were the key factors to promote the yield of $VB_{12}$. Thus, oxygen-supply level in the fermentation process was promoted by adjusting and improving the process, and the yield of $VB_{12}$ was enhanced greatly. Finally, the fermentation process was scaled up to a 120 m$^3$ industrial-scale fermenter in the same way. By adjusting parameters relevant to oxygen supply and OUR in the process, the final concentration of $VB_{12}$ was increased by 50% from 125 µg/ml before the process modification to 190 µg/ml after that.

The invention claimed is:

1. A biochemical reactor, wherein the biochemical reactor is equipped with an in-situ cell examination microscope,
   wherein the in-situ cell examination microscope comprises a main body of the microscope, an object lens, an observation entrance window, a sampling device and an exterior light source system,
   wherein the observation entrance window is arranged in front of the main body of the microscope, the sampling device is arranged in front of the observation entrance window, and an object lens and an exterior light source system are both arranged behind the observation entrance window in the main body of the microscope,
   wherein a reflecting prism is arranged between the exterior light source system and the object lens, a reflector is arranged behind the object lens while in front of the observation entrance window, an annular diaphragm plate is arranged in front of the reflecting prism, and a CCD or an area array image sensor is arranged above one side of the reflecting prism; and
   wherein the sampling device consists of a sampling piece, a flexible element and a movable device,
   wherein the sampling piece and a driving axle of the movable device are connected by the flexible element, and the space between the front end face of the sampling piece and the observation entrance window forms a sampling pool;
   wherein a living cell sensor is further arranged on a body of the biochemical reactor, and
   wherein the biochemical reactor is capable of measuring physiological metabolic parameters to optimize and scale up a fermentation process, and
   wherein the flexible element is compressible or stretchable to adjust a distance between the front end face of the sampling piece and the observation entrance window.

2. A biochemical reactor of claim 1, wherein the exterior light source system of the in-situ cell examination microscope consists of a light source, a condenser and a replaceable color filter, wherein the light source is a halogen lamp or a LED lamp, and light beams emitted by the lamp are focused by the condenser to give parallel beams from which beams in a desired band are obtained after they pass through the replaceable color filter.

3. A biochemical reactor of claim 1, wherein the movable device of the in-situ cell examination microscope consists of the driving axle, a connecting rod, a pulling rod for sampling and a flexible element, wherein the connecting rod equipped with the driving axle is connected to the pulling rod for sampling through a screw, the pulling rod for sampling and the flexible element are welded together at a position to give a sealed joint, and the main body of the microscope is connected to the other end face of the flexible element at a position by welding; or the movable device of the in-situ cell examination microscope consists of the driving axle, an electric motor and a sampling tube, wherein the sampling tube is connected to the front end of the microscope body, the electric motor is arranged at the back of the sampling tube, and the output axle of the electric motor is connected to the driving axle.

4. A biochemical reactor of claim 1, wherein the following components for process optimization and data scale-up are arranged on the body of the biochemical reactor:

a sensing system with apparatuses, instruments and sensors for detecting and controlling multiple parameters, a process pipeline system with installing supports, and an electric control cabinet with industrial personal computers and executing components.

5. A biochemical reactor of claim 4, wherein:

the sensing system comprises a temperature sensor, a pH sensor, a dissolved oxygen sensor, a whole-tank weight sensor, an exhaust gas $CO_2$ interface, an exhaust gas $O_2$ interface, a speed sensor, a pressure sensor and a defoaming sensor, wherein the multiple parameters include temperature, agitation speed, gas flow rate, tank pressure, defoaming, pH, dissolved oxygen concentration, real volume and weight of fermentation broth, amount of the feed including substrate, precursor, oil, and acidic/basic substance, exhaust gas $CO_2$ and exhaust gas $O_2$;

the process pipeline system with installing supports comprises a feed flask, a preheater, a stand for whole-tank weighing, a special support for sampling, a tank body assembly, a quick detachable bedplate, an electric motor, a pipe rack, an oil-water separator, a pressure reducing valve, a filter, a flowmeter, an air filter, a pressure gauge, a cooler, a pipe sight glass, a water heater, a sampling valve with no dead volume, a defoaming sensor interface, an exhaust gas $CO_2$ interface, an exhaust gas $O_2$ interface, a temperature sensor, a pH sensor interface and a DO sensor interface; and the electric control cabinet with industrial personal computers and executing components comprises a thermal mass flowmeter, a high-precision peristaltic pump, an electronic balance for supplementing substrate, a circulating pump, an electromagnetic valve, a digital-to-analog converter, an analog-to-digital converter, a local computer, an upper computer, a modem and a rare-earth motor.

6. An in-situ cell examination microscope, comprising a main body of the microscope, an object lens, an observation entrance window, a sampling device and an exterior light source system, wherein the observation entrance window is arranged in front of the main body of the microscope, the sampling device is arranged in front of the observation entrance window, and an object lens and an exterior light source system are both arranged behind the observation entrance window in the main body of the microscope, wherein a reflecting prism is arranged between the exterior light source system and the object lens, a reflector is arranged behind the object lens while in front of the observation entrance window, an annular diaphragm plate is arranged in front of the reflecting prism, and a CCD or an area array image sensor is arranged above one side of the reflecting prism;

wherein the sampling device consists of a sampling piece, a flexible element and a movable device, wherein the sampling piece and a driving axle of the movable device are connected by the flexible element, and the space between the front end face of the sampling piece and the observation entrance window forms a sampling pool, wherein a living cell sensor is further arranged on a body of the biochemical reactor, and wherein the flexible element is compressible or stretchable to adjust a distance between the front end face of the sampling piece and the observation entrance window.

7. A fermentation process using the biochemical reactor of claim 4, comprising the following steps:

(a) analysis of physiological metabolic parameters, and characteristics associated with the physiological metabolic parameters or combinations thereof, wherein the physiological metabolic parameters are selected from dissolved oxygen, oxygen uptake rate, pH, $CO_2$ evolution rate, respiratory quotient, the amount of living cells or cell morphology, metabolic product(s) to be measured, substrate consumption, or combinations thereof;

(b) comparing the physiological metabolic parameters, the characteristics associated with the physiological metabolic parameters or combinations thereof as measured in step (a) with those having predetermined values, choosing a biochemical reactor bearing measurements closest to the predetermined values, and thus determining a reactor that is optimized and scaled-up accordingly;

wherein the physiological metabolic parameters are defined in step (a).

8. A process of claim 7, wherein in step (a), the physiological metabolic parameters, the characteristics associated with the physiological metabolic parameters or combinations thereof are obtained by detecting several process control parameters of the biochemical reactor, wherein the several process control parameters are temperature, agitation speed, gas flow rate, tank pressure, defoaming, pH, dissolved oxygen concentration, real volume and weight of fermentation broth, amount of the feed including substrate, precursor, oil, and acidic/basic substance, exhaust gas $CO_2$ and exhaust gas $O_2$.

9. The in-situ cell examination microscope of claim 6, wherein the flexible element extends between a first end and a second end opposite the first end, the flexible element connects the sampling piece at the first end and connects the driving axle at the second end.

10. The biochemical reactor of claim 1, wherein the flexible element extends in a direction generally perpendicular to the observation entrance window.

11. The in-situ cell examination microscope of claim 6, wherein the flexible element extends in a direction generally perpendicular to the observation entrance window.

12. A biochemical reactor, wherein the biochemical reactor is equipped with an in-situ cell examination microscope, wherein the in-situ cell examination microscope comprises a main body of the microscope, an object lens, an observation entrance window, a sampling device and an exterior light source system, wherein the observation entrance window is arranged in front of the main body of the microscope, the sampling device is arranged in front of the observation entrance window, and an object lens and an exterior light source system are both arranged behind the observation entrance window in the main body of the microscope, wherein a reflecting prism is arranged between the exterior light source system and the object lens, a reflector is arranged behind the object lens while in front of the observation entrance window, an annular diaphragm plate is arranged in front of the reflecting prism, and a CCD or an area array image sensor is arranged above one side of the reflecting prism, wherein the sampling device consists of a sampling piece, a flexible element and a movable device, wherein the sampling piece and a driving axle of the movable device are connected by the flexible element, the space between the front end face of the sampling piece and the observation entrance window forms a sampling pool, the flexible element extends between a first end and a second end opposite the first end, and the flexible element connects the sampling piece at the first end and connects the driving axle at the second end, wherein a living cell sensor is further arranged on a body of the biochemical reactor, and wherein the flexible element is compressible or stretchable to adjust a distance between the front end face of the sampling piece and the observation entrance window.

* * * * *